US012700248B2

(12) United States Patent
　　Kozlowski et al.

(10) Patent No.: US 12,700,248 B2
(45) Date of Patent: Aug. 4, 2026

(54) ASSESSING HETEROGENEITY OF FEATURES IN DIGITAL PATHOLOGY IMAGES USING MACHINE LEARNING TECHNIQUES

(71) Applicant: Genentech, Inc., South San Francisco, CA (US)

(72) Inventors: Cleopatra Kozlowski, Woodside, CA (US); Reheman Baikejiang, South San Francisco, CA (US)

(73) Assignee: GENENTECH, INC., South San Francisco, CA (US)

( * ) Notice: Subject to any disclaimer, the term of this patent is extended or adjusted under 35 U.S.C. 154(b) by 527 days.

(21) Appl. No.: 18/094,850

(22) Filed: Jan. 9, 2023

(65) Prior Publication Data

US 2023/0162515 A1　May 25, 2023

Related U.S. Application Data

(63) Continuation of application No. PCT/US2021/041578, filed on Jul. 14, 2021.

(Continued)

(51) Int. Cl.
　　*G06V 20/69*　　(2022.01)
　　*G06V 10/77*　　(2022.01)
　　(Continued)

(52) U.S. Cl.
　　CPC ........ *G06V 20/695* (2022.01); *G06V 10/7715* (2022.01); *G06V 10/774* (2022.01);
　　(Continued)

(58) Field of Classification Search
　　USPC ........................................... 382/133
　　See application file for complete search history.

(56) References Cited

U.S. PATENT DOCUMENTS

2012/0082362 A1 * 4/2012 Diem ..................... G16Z 99/00
　　　　　　　　　　　　　　　　　　　　382/133
2017/0358079 A1 * 12/2017 Gillies ................... G16H 15/00
　　　　　　　　　　(Continued)

FOREIGN PATENT DOCUMENTS

CN　　　106096654 A　　11/2016
WO　　2015069827 A2　　5/2015
　　　　　(Continued)

OTHER PUBLICATIONS

International Preliminary Report on Patentability, issued Jan. 17, 2023, for PCT Application No. PCT/US2021/041578, filed Jul. 14, 2021, 7 pages.

(Continued)

*Primary Examiner* — Chineyere Wills-Burns
*Assistant Examiner* — Aaron Timothy Bonansinga
(74) *Attorney, Agent, or Firm* — MORRISON & FOERSTER LLP

(57) ABSTRACT

In one embodiment, a method includes, receiving a digital pathology image of a tissue sample and subdividing the digital pathology image into a plurality of patches. For each patch of the plurality of patches, the method includes identifying an image feature detected in the patch and generating one or more labels corresponding to the image feature identified in the patch using a machine-learning model. The method includes determining, based on the generated labels, a heterogeneity metric for the tissue sample. The method includes generating an assessment of the tissue sample based on the heterogeneity metric.

19 Claims, 15 Drawing Sheets

Related U.S. Application Data

(60) Provisional application No. 63/052,297, filed on Jul. 15, 2020.

(51) Int. Cl.
| | |
|---|---|
| *G06V 10/774* | (2022.01) |
| *G16B 20/00* | (2019.01) |
| *G16B 40/20* | (2019.01) |

(52) U.S. Cl.
CPC ........... *G06V 20/698* (2022.01); *G16B 20/00* (2019.02); *G16B 40/20* (2019.02)

(56) References Cited

U.S. PATENT DOCUMENTS

| | | | | |
|---|---|---|---|---|
| 2018/0121759 A1* | 5/2018 | Gabrani | ................ | G06T 7/0012 |
| 2018/0333140 A1* | 11/2018 | Wodlinger | ............. | A61B 8/488 |
| 2019/0042826 A1* | 2/2019 | Chang | ........................ | G06T 7/11 |
| 2019/0080450 A1* | 3/2019 | Arar | ........................ | G06T 7/194 |
| 2019/0113423 A1* | 4/2019 | Goodman | ................ | G01N 1/36 |
| 2020/0184643 A1* | 6/2020 | Coudray | ............... | G06T 7/0012 |
| 2020/0302603 A1* | 9/2020 | Barnes | ................. | G06T 7/0012 |
| 2020/0342597 A1* | 10/2020 | Chukka | ................... | G06T 7/194 |
| 2021/0003555 A1* | 1/2021 | Ferte | ................. | G01N 33/5005 |
| 2021/0090694 A1* | 3/2021 | Colley | ................... | G16B 30/00 |
| 2021/0192737 A1* | 6/2021 | Zhou | ....................... | G06T 7/285 |
| 2021/0193323 A1* | 6/2021 | Jain | ........................ | G16H 50/20 |

FOREIGN PATENT DOCUMENTS

| | | |
|---|---|---|
| WO | 2019108695 A1 | 6/2019 |
| WO | 2019110567 A1 | 6/2019 |

OTHER PUBLICATIONS

International Search Report and Written Opinion, mailed Nov. 5, 2021, for PCT Application No. PCT/US2021/041578, filed Jul. 14, 2021, 10 pages.

Baine, M.J. et al. (Apr. 2018). "Histology Significantly Affects Recurrence and Survival Following SBRT for Early Stage Non-Small Cell Lung Cancer," Lung Cancer 118:20-26.

Tian, S. (Nov. 2017). "Classification and Survival Prediction for Early-Stage Lung Adenocarcinoma and Squamous Cell Carcinoma Patients," Oncol Lett. 14(5):5464-5470.

Wood, N.M. et al. (Mar. 2017, e-pub. Dec. 22, 2016). "A Histologic Basis for the Efficacy of SBRT to the Lung," Journal of Thoracic Oncology 12(3):510-519.

* cited by examiner

250

270 Patch-based Signature

275 Compute heterogeneity metric

Heterogeneity Metric

280 Subject Assessment

Visualization Tool 260

205 Digital Pathology Image

Patches with labels

255a KRAS

255b EGFR

255c KRAS

255n EGFR

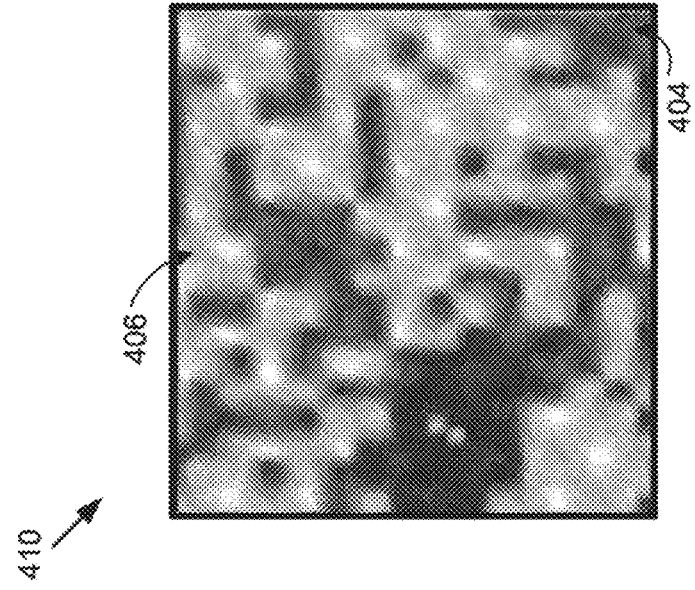
FIG. 4A

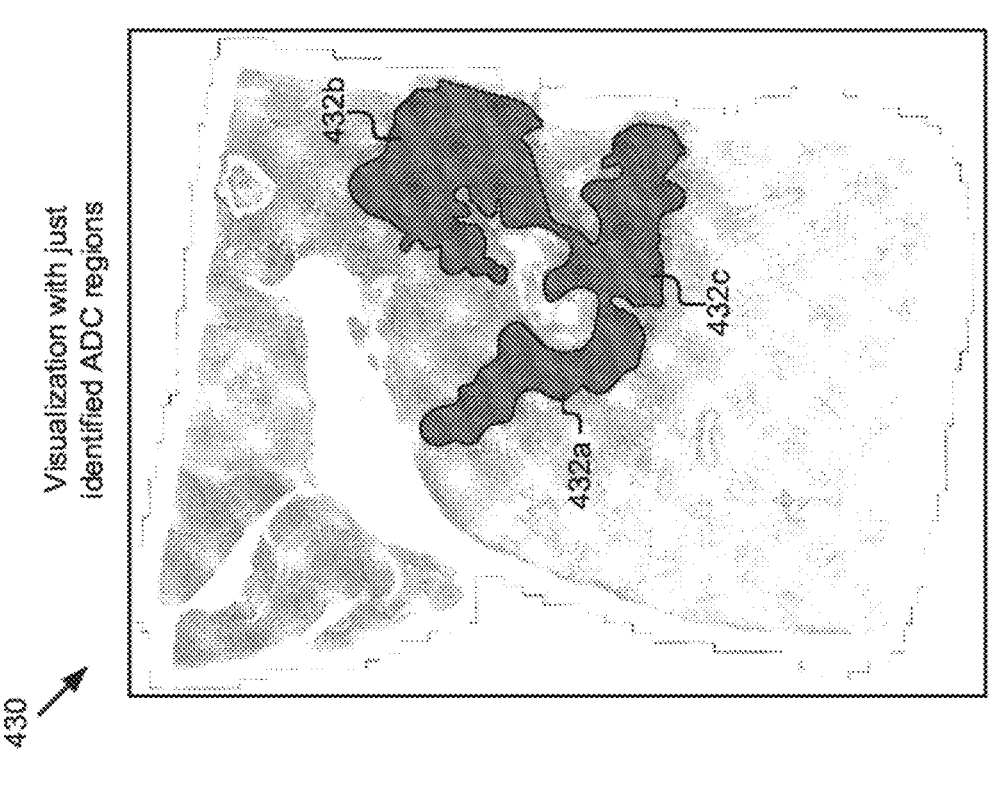
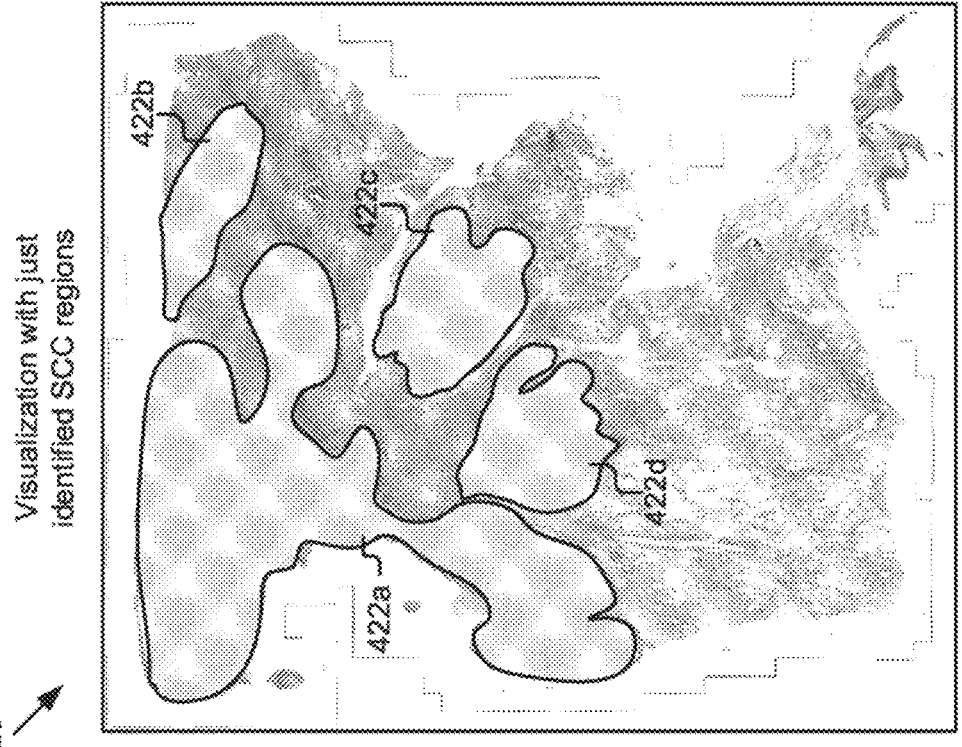
*FIG. 4B*

700

710 — Receive a digital pathology image of a tissue sample

715 — Subdivide the digital pathology image into patches

720 — Identify and classify image feature(s) detected in each of the patches

725 — Generate label(s) for identified feature(s) using a machine-learning model 730 — Generate a patch-based signature depicting visualization of image features in the digital pathology image 735 — Compute a heterogeneity metric based on generated labels 740 — Generate a subject assessment based on the heterogeneity metric 745 — Provide the subject assessment to a user 750 — Receive feedback regarding provided assessment 755 — Update machine-learning model based on received feedback

*FIG. 7*

ASSESSING HETEROGENEITY OF FEATURES IN DIGITAL PATHOLOGY IMAGES USING MACHINE LEARNING TECHNIQUES

PRIORITY

This application is a continuation of International Application No. PCT/US2021/041578, filed on Jul. 14, 2021, which claims the benefit, under 35 U.S.C. § 119 (e), of U.S. Provisional Patent Application No. 63/052,297, filed 15 Jul. 2020, which is incorporated herein by reference.

TECHNICAL FIELD

This disclosure generally relates to classifying digital pathology images and assessing heterogeneity of features detected in whole slide images.

BACKGROUND

Adenosquamous carcinomas of the lung carry a poor prognosis compared to other non-small cell lung cancers (NSCLC). Adenocarcinoma (ADC) and squamous cell carcinoma (SCC) are common types of NSCLC. Adenosquamous carcinoma (ASC) has features of both ADC and SCC in the same tumor. The incidence of ASC varies between studies but is estimated to account for 0.4 to 4% of all lung cancers. Diagnosis of these cancers depends on several factors including adequate sampling of the tumor, careful review, and objective interpretation of histologic criteria.

Certain gene mutations are linked to NSCLC or other types of cancers. Having one or more of these mutations could affect the type of treatment that a doctor recommends. As such, identifying these different gene mutations in patients can affect treatment and patient outcomes. Gene mutations that are commonly associated with NSCLC include tumor protein 53 (TP53) mutation, Kirsten rat sarcoma viral oncogene homolog (KRAS) mutation, epidermal growth factor receptor (EGFR) mutation, and anaplastic lymphoma kinase (ALK) mutation.

Current techniques or approaches for identifying histologies (e.g., ADC cancer regions, SCC cancer regions, etc.) require manual identification in digital pathology images (e.g., whole slide images) by pathologists or other trained specialists. Manual identification is time consuming, laborious, and sometimes bound to human errors. Also, it is often not possible to manually identify tumor mutations from digital pathology images alone. Accordingly, a desire exists for an automated technique or approach for identifying features, including histologies, mutations, or other features of interest, in digital pathology images with respect to NSCLC, other cancers, and other conditions. In addition, a desire exists for assessing heterogeneity of these features in patients with particular conditions (e.g., particular cancers) that would lead to a better understanding of tumor biology and patients' responsiveness to various treatments.

SUMMARY OF PARTICULAR EMBODIMENTS

In particular embodiments, a computer-implemented method includes receiving a digital pathology image of a tissue sample and subdividing the digital pathology image into a plurality of patches. The digital pathology image of the tissue sample may be a whole-slide scanned image of a tumor sample from a patient diagnosed with non-small cell lung cancer (NSCLC). In particular embodiments, the digital pathology image or the whole slide image is a hematoxylin and eosin (H&E) stained image. The method includes identifying, for each patch, an image feature detected in the patch and generating one or more labels corresponding to the image feature identified in the patch using a machine-learning model. The machine-learning model may be a deep-learning neural network. In one embodiment, the image features include histologies and the one or more labels applied to the patch include adenocarcinoma (ADC) and squamous cell carcinoma (SCC) cancer regions. In another embodiment, the image features indicate gene mutations or variants and the one or mote labels applied to the patch include Kirsten rat sarcoma viral oncogene homolog (KRAS) mutation, epidermal growth factor receptor (EGFR) mutation, anaplastic lymphoma kinase (ALK) mutation, or tumor protein 53 (TP53) mutation. The method includes determining a heterogeneity metric for the tissue sample based on the generated labels. If the tissue sample is represented by patches with a mixture of different labels, it is considered heterogeneous. The heterogeneity metric may be used to evaluate the extent of heterogeneity of the identified image features and corresponding labels in the tissue sample. The method further includes generating an assessment of the tissue sample based on the heterogeneity metric. A determination as to whether a subject is eligible for a clinical trial in testing a medical treatment for a particular medical condition may be made based on the assessment. Also, one or more treatment options may be determined for the subject based on the assessment.

In particular embodiments, a digital pathology image processing system can output various visualizations, such as patch-based image signatures, indicating extent of heterogeneity of the identified features and corresponding labels. The patch-based signatures can be used by the pathologists to visualize the identified image features or to evaluate the machine-learning model. Also, the patch-based signatures can assist the pathologists in diagnosis or assessment of the subject or review of an initial assessment. A patch-based signature may be generated based on the identified image features and may depict a visualization of the identified image features in the tissue sample, such as displaying each of the labels corresponding to the identified image features in different color coding. In one embodiment, the patch-bused signature may be generated using a saliency mapping technique. In particular embodiments, the patch-based signature is a heatmap that includes a plurality of regions. Each region of the plurality of region is associated with an intensity value. One or more regions of the plurality of regions are further associated with a predicted label of the patch of the digital pathology image.

In particular embodiments, the digital pathology image processing system can train a machine-learning model (e.g., deep-learning neural network) to identify image features and generate labels corresponding to the identified image features (e.g., histologies, mutations, etc.) shown in a plurality of patches from a digital pathology image. Training the machine-learning model may include accessing a plurality digital pathology images associated with a plurality of subjects, respectively (e.g., tissues samples from NSCLC patients), identifying a tumor region in each of the plurality of digital pathology images, subdividing the plurality of digital pathology images into a set of training patches, where each training patch in the set is classified with one or more features and annotated with one or more ground-truth labels corresponding to the one or more features, and using classified set of patches with ground-truth labels corresponding to the features shown in the patches to train the machine-learning model. The ground-truth labels are provided by a clinician.

In particular embodiments, the digital pathology image processing system can further test an accuracy or verify training of the machine-learning model and update the model based on the verification. Testing and updating the machine-learning model includes accessing a particular digital pathology image of a particular subject, subdividing the particular digital pathology image into a set of patches, identifying and classifying second image features detected within the patches, generating a set of predicted labels corresponding to the identified second image features for the set of patches using the trained machine-learning model, comparing the generated set of predicted labels with ground-truth labels associated with the set of patches, and updating the machine-learning model based on the comparison. Updating the machine-learning model may include further training the machine-learning model.

Using a machine-learning model or deep-learning neural network to classify image features (e.g., histologies, gene mutations, etc.) and generate corresponding labels (e.g., mutation type, histology subtype, etc.) in digital pathology (e.g., H&E stained) images is particularly advantageous in a number of ways. Some of the advantages may include, for example and without limitation. 1) reducing the burden on users (e.g., pathologists, doctors, clinical specialist, etc.) from manually evaluating thousands of whole slide images and identifying features in each of these images for study, 2) expediting the overall image classification and evaluation process and, once the model is sufficiently trained, there may in fact be fewer error or chances of errors that may sometimes be introduced in the manual classification and evaluation by humans, 3) helping to identify novel biomarkers or features that were previously unknown, 4) studying the role of heterogeneity in patient responses to therapies, and 5) utilizing images resulting from relatively inexpensive and rapid process of H&E staining rather than relying on expensive and time-consuming DNA sequencing for certain types of analysis.

The embodiments disclosed herein are only examples, and the scope of this disclosure is not limited to them. Examples herein may be described with respect to particular types of cancers (e.g., lung cancer, prostate cancer, etc.). These descriptions are by way of example only and not limitation, as the techniques for application to the specific cancers discussed could be applied to other types of cancers and/or other conditions without requiring significant modification or deporting from the techniques of this disclosure. Particular embodiments may include all, some, or none of the components, elements, features, functions, operations, or steps of the embodiments disclosed herein. Embodiments according to the invention are in particular disclosed in the attached claims directed to a method, a storage medium, a system and a computer program product, wherein any feature mentioned in one claim category, e.g., method, can be claimed in another claim category, e.g., system, as well. The dependencies or references back in the attached claims are chosen for formal reasons only. However any subject matter resulting from a deliberate reference back to any previous claims (in particular multiple dependencies) can be claimed as well, so that any combination of claims and the features thereof are disclosed and can be claimed regardless of the dependencies chosen in the attached claims. The subject-matter which can be claimed includes not only the combinations of features as set out in the attached claims but also any other combination of features in the claims, wherein each feature mentioned in the claims can be combined with any other feature or combination of other features in the claims. Furthermore, any of the embodiments and features described or depicted herein can be claimed in a separate claim and/or in any combination with any embodiment or feature described or depicted herein or with any of the features of the attached claims.

BRIEF DESCRIPTION OF THE DRAWINGS

FIGS. 4A-4B illustrate example visualizations that may be generated based on image features and corresponding labels identified using a machine-learning model.

FIG. 7 illustrates an example method for identifying features in a digital pathology image using a machine-learning model and generating a subject assessment based on heterogeneity of the identified features in the digital pathology image.

DESCRIPTION OF EXAMPLE EMBODIMENTS

Figure 1A:
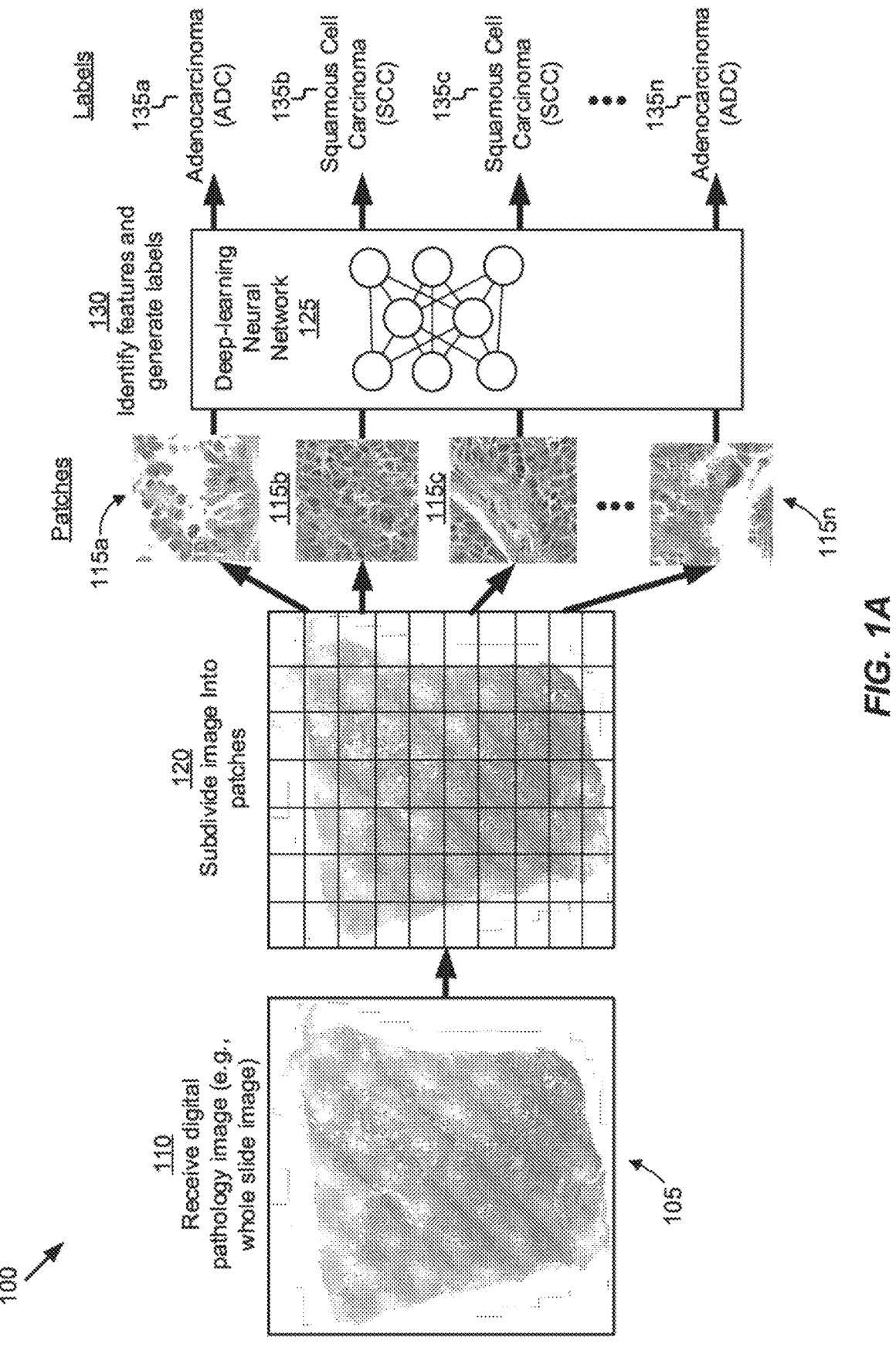
FIGS. 1A-1B illustrate an example process for identifying features in a digital pathology image using a machine-learning model and generating a subject assessment based on heterogeneity of the identified features in the digital pathology image.

The present embodiments include an automated method for detecting various features, such as histologies and mutations, in digital pathology images of samples taken from a subject. The present embodiments further include automated methods for assessing heterogeneity of these features depicted in the digital pathology images for generating assessments of a condition of the subject, such as diagnosis and prognosis of certain conditions, such as cancer, and recommendations for treatments for certain conditions. In particular embodiments, an exemplary method includes using a machine-learning model (e.g., a deep-learning neural network) to produce a whole-slide prediction of image features, generating labels for patches subdivided from the whole slide corresponding to these features, computing a heterogeneity metric based on the labels, and generating a subject assessment, e.g., a diagnosis or prognosis, based on the computed heterogeneity metric. In some embodiments, a patch-based signature (e.g., a heatmap, statistical correlation, count, threshold, encoding, etc.) may be created and used to assess the machine-learning model in identifying features within a tissue sample. The present embodiments may include developing such patch-based signatures using neural networks and developing evaluation criteria of the patch-based signatures using neural networks. These embodiments may help standardize and expedite correct identification of heretofore difficult to identify subtypes and combinations of presenting criteria and, as a result, lead to better targeted therapies. In addition, an automated technique to quantify the relative contributions of image features (e.g., corresponding to histologies) in heterogeneous tumors would lead to a better understanding of tumor biology.

In particular embodiments, training a machine-learning model or neural network for classifying image features and generating labels may include training the model based on image data of tissue samples from a plurality of patients with certain condition types, such as tissue samples from NSCLC patients. Training samples may be scanned at a specified resolution, and the image data may include a tumor area identified by a pathologist. Each slide tumor area may be divided into smaller image patches. For example, a patch may have an area of 512×512 pixels, where the original image can be on the order of 100.000×100.000 pixels. A classifier for tissue patches, to identify and classify the image features shown therein, may be developed using the whole-slide level labels. The classifier may be derived from a convolutional neural network (CNN) trained using transfer learning and weakly-supervised learning.

Once the machine learning model (e.g., deep learning neural network) is sufficiently trained, the model may be applied to perform a patch-level prediction on unseen test images or slides. The model may output results, including a whole-slide diagnosis performed by choosing a most common feature (e.g., histology) predicted among all patches extracted for each slide. In some embodiments, a patch-based image signature may be created to visualize or represent an extent of heterogeneity of the detected features (e.g., histologies) within a single tissue sample in a human interpretable form. The embodiment may further include outputting visualizations, including depictions of the patch-based image signature, network and/or image features that contribute to the patch level classification decision, etc.

Figure 1B:
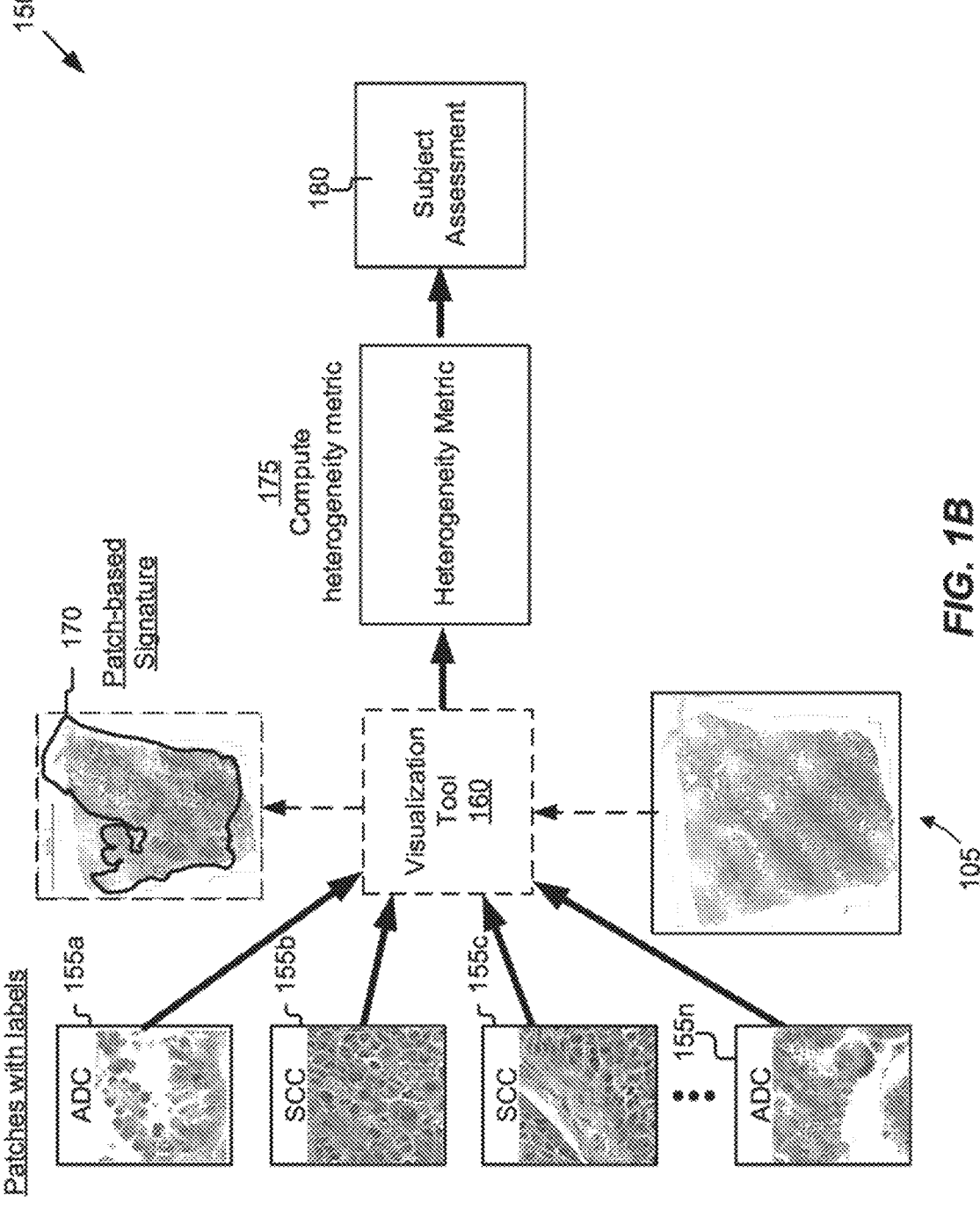
Figure 2A:
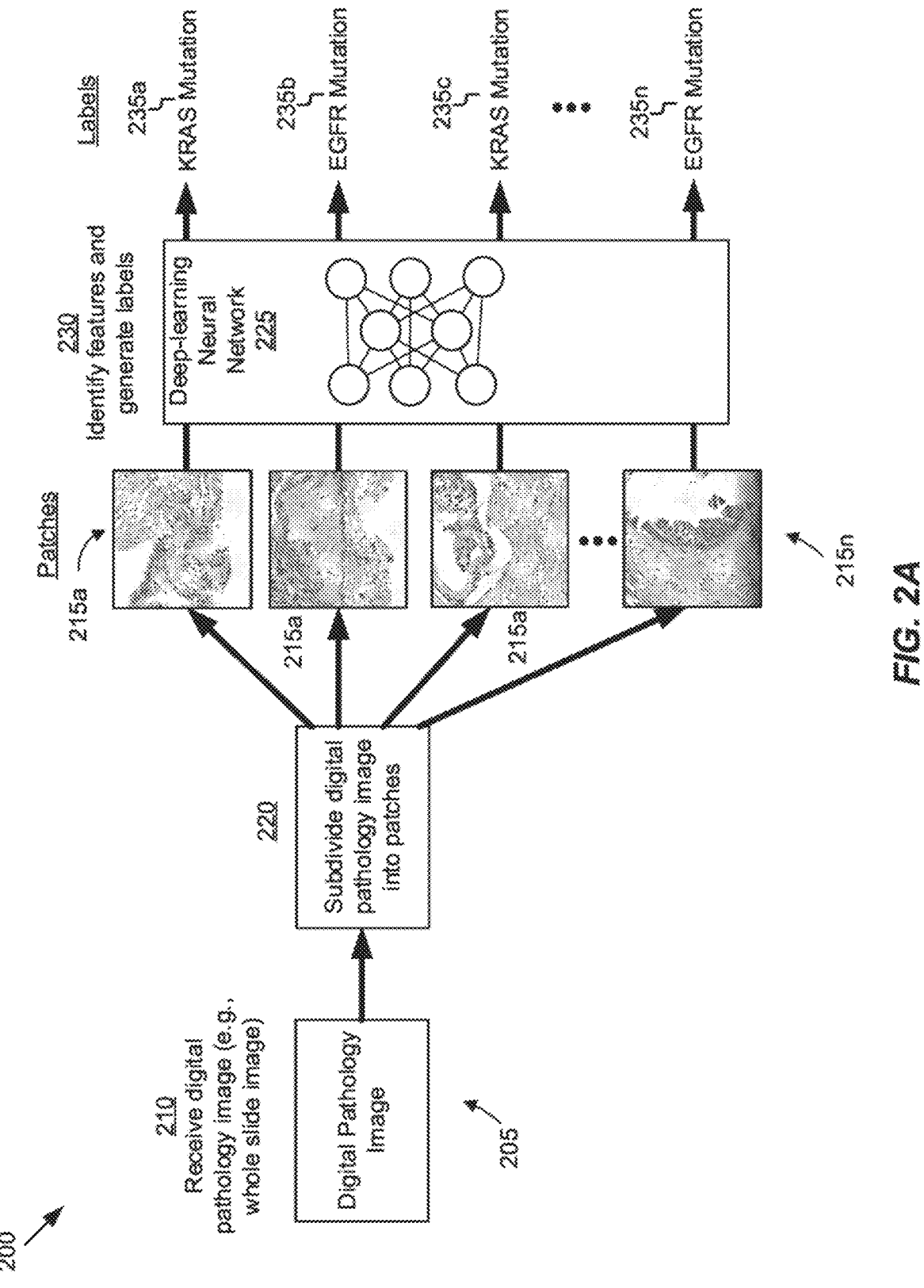
FIGS. 2A-2B illustrate another example process for identifying features in a digital pathology image using a machine-learning model and generating a subject assessment based on heterogeneity of the identified features in the digital pathology image.
Figure 2B:
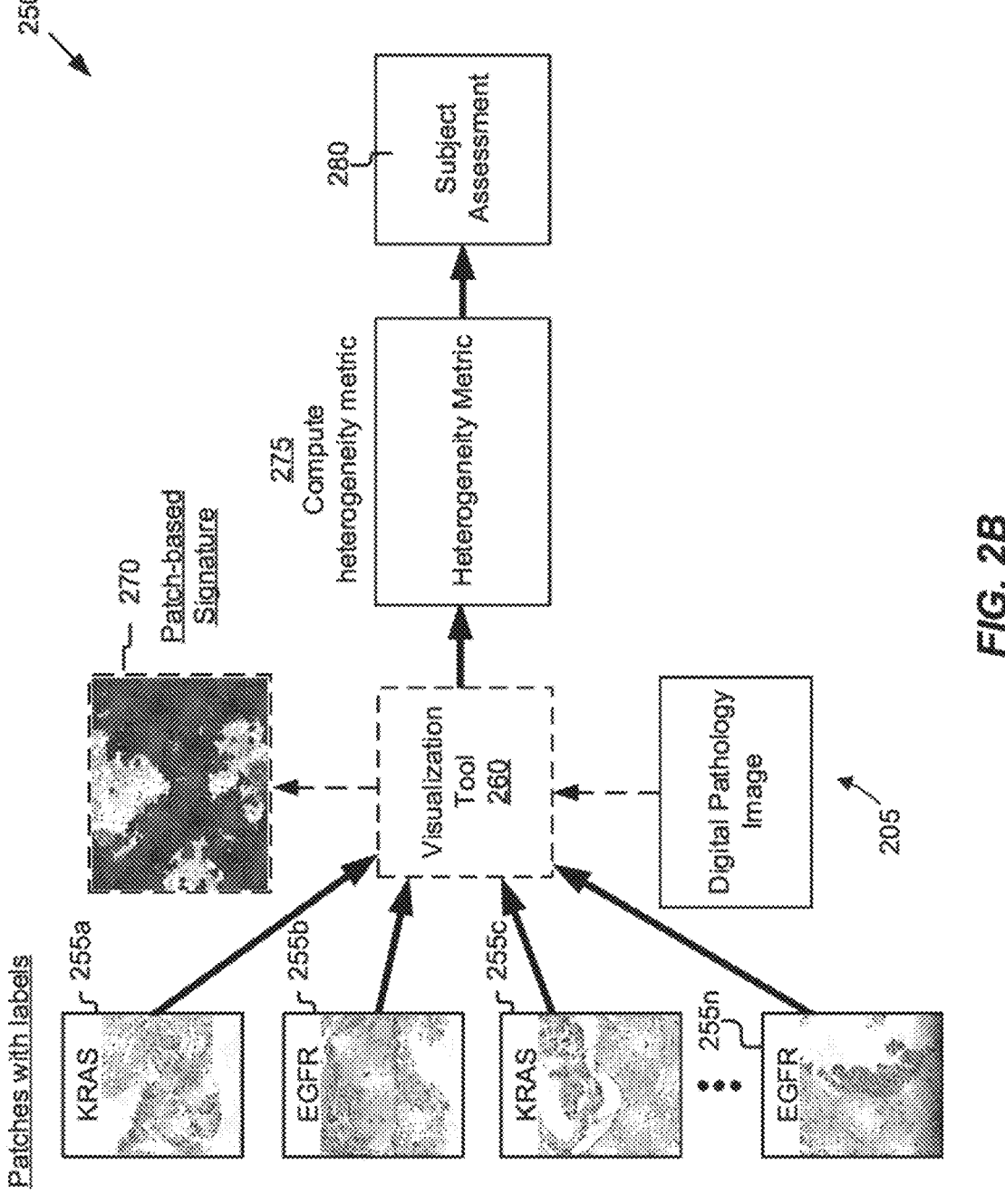

Using machine-learning techniques to identify features, including histologies or mutations, in digital pathology images (e.g., H&E stained images) will now be described with respect to FIGS. 1A-1B and 2A-2B. In particular, FIGS. 1A-1B illustrate and describe an embodiment for identifying or extracting histologies, from patches of an example digital pathology image using a deep-teaming neural network and evaluating heterogeneity of the extracted histologies for diagnosing condition of lung cancer in a subject or patient. FIGS. 2A-2B illustrate and describe an embodiment for identifying mutations or gene variants from patches of an example digital pathology image using a deep-learning neural network and evaluating heterogeneity of the identified mutations for subject assessment. It should be noted that some of the description in these FIGS. 1A-1B and 2A-2B may overlap (e.g., process for image classification and heterogeneity computation), however the features, labels, heterogeneity metric, and subject assessment that are determined or generated in each of FIGS. 1A-1B and 2A-2B are different. Each of these figures is described in detail below.

Figure 3:
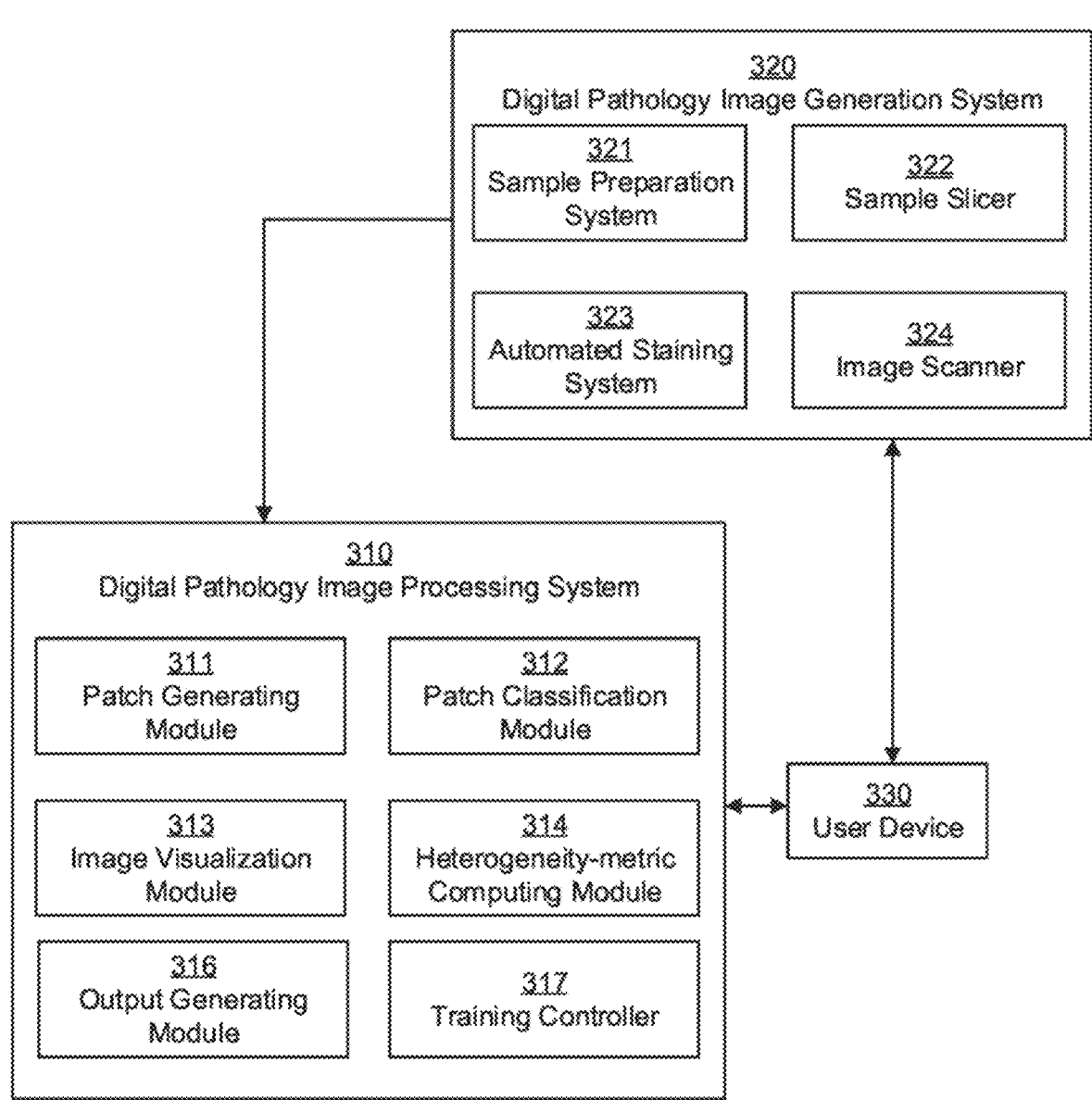
FIG. 3 illustrates an example network including a digital pathology image processing system and digital pathology image generation system.

FIGS. 1A-1B illustrate example processes 100 and 150 for identifying features in a digital pathology image using a machine-learning model and generating a subject assessment based on heterogeneity of the features in the digital pathology image, respectively. Specifically, FIGS. 1A-1B illustrate identifying or extracting features, e.g., histologies, front patches of an example digital pathology image using a deep-learning neural network and evaluating heterogeneity of the extracted histologies for diagnosing condition of lung cancer in a subject or patient. Identifying mixed histologic subtypes may enable better selection of patients/subjects responsive to drug treatment and elucidate the biological mechanism leading to tumor heterogeneity. FIG. 3 illustrates a network 300 of interacting computer systems that can be used, according to some embodiments described heroin, for extracting histologies using deep-learning neural networks and evaluating heterogeneity of the extracted histologies. As illustrated in FIG. 1A, at 110, a digital pathology image processing system 310 receives a digital pathology image 105 of a tissue sample. In particular embodiments, the digital pathology image of the tissue sample can be a whole-slide image of a sample from a subject or patient diagnosed with non-small cell lung cancer. In a first embodiment, the digital pathology image or the whole-slide image discussed herein is a H&E stained image or can be obtained from a H&E preparation of a tumor sample from the patient diagnosed with rum-small cell lung cancer. The advantage of using the H&E stained image is that it is relatively fast and cheap to obtain, especially compared to other techniques, such as DNA sequencing, which are an expensive and time-consuming process for identifying certain histologies. It should be understood that images produced through other staining and imaging techniques may also be used without deviating from the teachings of this disclosure. The digital pathology image processing system 310 can receive the digital pathology image or the whole slide image 105 from a digital pathology image generation system 320 or one or more components thereof. An another example, the digital pathology image processing system 310 can receive the digital pathology image 105 from one or more user devices 330. User device 330 can be a computer used by a pathologist or clinician connected via one or more networks to the digital pathology image processing system 310. The user of the user device 330 can use the user device 330 to upload the digital pathology image 105 or to direct one or more other devices to provide the digital pathology image 105 to the digital pathology image processing system 310.

In certain embodiments, although not shown in FIG. 1A, the digital pathology image processing system 310 may perform a tumor lesion segmentation on the image 110. For instance, a tumor region (e.g., disease area) may be identified in the image 110. In one embodiment, the digital pathology image processing system 310 may identify a tumor region with the help of a user. For instance, the digital pathology image processing system 310 automatically identifies a tumor region using a separate tumor segmentation algorithm or one or more machine-learning techniques. For instance, a machine-learning model may be trained based on pre-labeled or pre-annotated tumor regions in a set of digital pathology images by human experts. In some embodiments the tumor region may be manually selected by a pathologist, a doctor, a clinical specialist, an expert in diagnosing lung cancers (or another cancer of interest relevant to the tissue sample), etc. Performing the tumor lesion segmentation is advantageous as it eliminates irrelevant portions (e.g., blank regions) of the digital pathology image 110 that do not contribute to the evaluation of the features and ultimately reduce the prevalence of useful signals.

At 120, the digital pathology image processing system 310, for example using a patch generating module 311, subdivides the digital pathology image 105 (with identified tumor region) into a plurality of patches 115*a*, 115*b*, 115*c*, . . . 115*n* (also individually or collectively herein referred to as 115). Subdividing the image 105 may include, in some instances, tiling the image in a grid-structure format into small image tiles or patches, as shown in FIG. 1A. Although illustrated as occurring after tumor lesion segmentation, in particular embodiments, the tumor lesion segmentation process can occur after subdividing the image into patches.

At 130, the digital pathology image processing system 310, for example using a patch classification module 312, identifies one or mote image features within each of the patches and generates a plurality of labels 135*a*, 135*b*, 135*c*, . . . 135*n* (also individually or collectively herein referred to as 155) for the plurality of patches 115 corresponding to the identified image features using a deep learning neural network 125. In some embodiments, by identifying image features, as discussed elsewhere herein, the digital pathology image processing system 310 can identify or classify underlying tissue structures within a tissue sample. Each label 135 may indicate, identify, or represent a particular image feature, such as type of non-small cell lung cancer (NSCLC). As an example, for patch 115*a*, the patch classification module 312 generates a corresponding label 135*a* indicating that one or more image features depicted in the patch 115*a* are associated with adenocarcinoma (ADC), for patch 115*b*, the patch classification module 312 generates a corresponding label 135*b* indicating that one or more image feature depicted in the patch 115*b* are associated with squamous cell carcinoma (SCC), for patch 115*c*, the patch classification module 312 generates a corresponding label 135*c* indicating that one or more image features depicted in the patch 115*b* are associated with SCC, and for patch 115*n*, the patch classification module 312 generates a corresponding label 135*n* indicating that one or more image features depicted in the patch 115*n* are associated with ADC. Although only two types of labels, ADC and SCC are illustrated in FIG. 1A, it should be noted that other types of labels for other features in tissue structures may be identified using the deep-learning neural network 125.

In particular embodiments, the deep-learning neural network 125 discussed herein is a convolutional neural network that may be trained based on Inception V3 and Resnet18 architecture using transfer learning and weakly-supervised learning techniques. It should be understood that other learning techniques for training the deep-learning neural network 125 are also possible and within the scope of the present disclosure. The training of the deep-learning neural network 125 for classifying image patches based on histologies identified within the image patches is discussed in detail below in reference to at least FIGS. 5A-5B and 8.

FIG. 1B illustrates a process 150 for evaluating heterogeneity of the histologies identified in the digital pathology images (e.g., in the patches of the digital pathology image) for subject assessment bused on the labels 135 generated through the process 100 in FIG. 1A. It should be noted that similar to FIG. 1A, references will be made to FIG. 3 for various computing components or modules that perform their respective operations in the process 150. As depicted, the digital pathology image processing system 310, for example using an image visualization module 313, may optionally feed the labelled patches (e.g., patches and their corresponding histologies) into an optional visualization tool or application 160. For instance, the image visualization module 313 may feed, along with the digital pathology image 105, a patch labeled ADC 155*a*, a patch labeled SCC 155*b*, a patch labelled SCC 155*c*, and a patch labelled ADC 155*n* into the visualization tool 160. In some embodiments, the image visualization module 313 and the visualization tool 160 are combined or work together as a single component. In other embodiments, the image visualization module 313 and the visualization tool 160 are separate components.

Figure 4C:
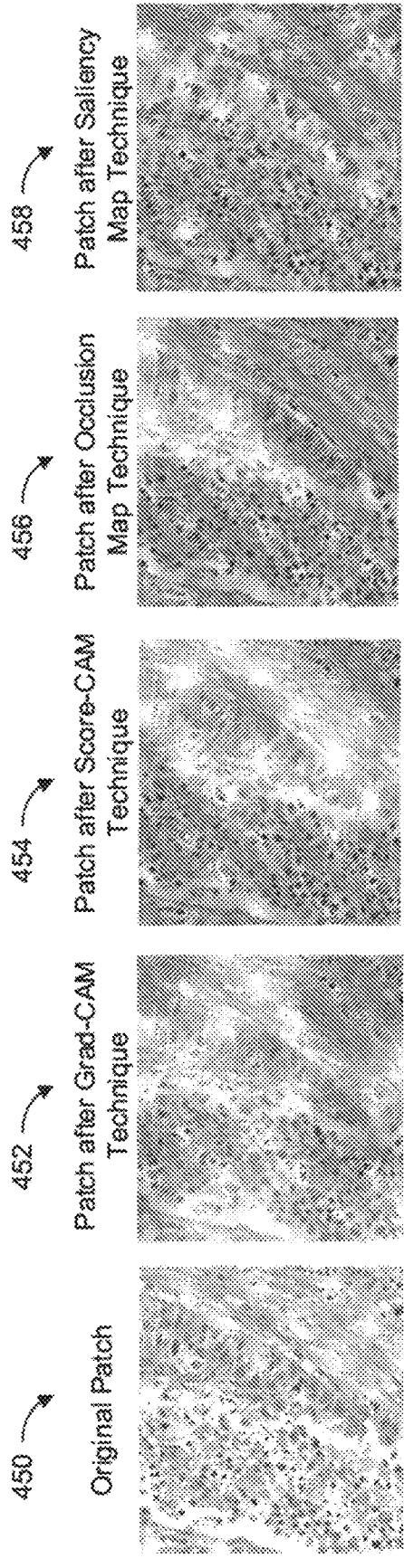
FIG. 4C illustrates visualizing an example digital pathology image using different visualization techniques.

In some embodiments, the optional visualization tool 160 using the labelled patches 155 and the overall digital pathology image or whole slide image 105 can generate an optional patch-based signature (e.g., heatmap, region overlays) 170 for the digital pathology image. It should be noted that the visualization tool 160 and patch-based signature 170 are shown with dotted lines to indicate that they are optional parts or components of the process 150 and may or may not be used in evaluating heterogeneity discussed herein. In particular embodiments, the patch-based signature 170 may depict a visualization of the histologies within the tissue sample. The visualization may include displaying the histologies in different color coding, as depicted in FIGS. 4A-4B. By way of an example, without limitation, visualizing different histologies in a tissue sample through a patch-based signature may include displaying ADC cancer regions in blue color, SCC cancer regions in given color, etc. In particular embodiments, the digital pathology image processing system 310, for example using the image visualization module 313, may use different visualization techniques to generate the patch-based signature discussed herein. For instance, the image visualization module 313 may use one or more of a gradient-weighted class activated mapping (Grad-CAM) technique, a score weighted class activated mapping (score-CAM) technique, an occlusion mapping technique, and a saliency mapping technique to generate the visualization. Different visualization techniques are shown and discussed below in reference, to FIG. 4C. In particular embodiments, the image visualization module 313 uses the saliency mapping technique to generate the patch-based signature 170.

At 175, the digital pathology image processing system 310, for example using a heterogeneity-metric computing module 314, computes a heterogeneity metric of the histologies identified in or extracted from the digital pathology image (e.g., through the patches) using the labelled patches 155 (e.g., patches and their corresponding labels). The heterogeneity metric may be able to assess heterogeneity of histologies in cancer. The heterogeneity metric may include a quantifiable measure of the level or degree of heterogeneity of the histologies. In particular embodiments, the heterogeneity metric may quantify a relative proportion of each histology with respect to other histologies in a given tissue sample. By way of an example, without limitation, the heterogeneity metric may indicate, for ADC and SCC histologies identified in FIG. 1A, the percentage of each of the ADC and SCC cancer regions in the tissue sample (e.g., non-small cell lung cancer image of the patient). Stated differently, the heterogeneity metric may indicate how many total ADC cancer regions are present with respect to the total SCC cancer regions in the tissue sample. For example, the heterogeneity metric may indicate that there are total 392 ADC and 150 SCC cancer regions in the given tissue sample. As another example, the heterogeneity metric may indicate the inter-relatedness of the ADC and SCC cancer regions to identify how distributed the regions are in the sample.

In an alternative embodiment, the heterogeneity-metric computing module 314 can compute a heterogeneity metric based on a patch-based signature discussed herein. For instance, the heterogeneity-metric module 314 may receive the patch-based signature from the image visualization module 313 and compute a heterogeneity metric using information depicted in the patch based signature. As an example, the patch-based signature may depict the distribution or proportion of each of the labels (e.g., ADC, SCC) within a tissue sample (as shown for example in FIG. 4A) and the heterogeneity-metric compute module 314 may use this distribution information of the patch-based signature to compute a heterogeneity metric. In some embodiments, the patch-based signature may correspond to a patch-level assessment of the heterogeneity of the features (e.g., histologies). The patch-based signature may be unique to the digital pathology image or may he understood to relate to patterns or classification of the heterogeneity of the features of the digital pathology image.

The digital pathology image processing system 310, for example using an output generating module 316, generates an output based on the heterogeneity metric. In particular embodiments, the output can include a subject assessment 180 based on the computed heterogeneity metric. The subject assessment can include, for example, a subject diagnosis, subject prognosis, or treatment recommendation as applicable for the particular use case of the operator. For instance, based on the heterogeneity metric indicating how heterogenous the image features (e.g., histologies) and/or labels (e.g., ADC cancer regions, SCC cancer regions) are in a given tissue sample, the output generating module 316 may generate an appropriate assessment of the given tissue sample. As an example, the assessment may include a severity of the lung cancer in a patient based on an amount, of ADC and SCC cancer regions present in the tissue sample of the patient. As another example, the assessment may include best treatment option(s) for lung cancer in a patient based on the existence or heterogeneity of ADC and SCC cancer regions present in the tissue sample of the patient. In some embodiments, the output generating module 316 may provide the subject assessment 180 for display to a user, such as a pathologist, a doctor, a clinical specialist, an expert in diagnosing lung cancers, an operator of the digital pathology image processing system 310, etc. The subject assessment 180 can also be provided to one or more user devices 330. In some embodiments, the subject assessment 180 can be used to predict subject's responsiveness to various treatments, to predict the appropriateness of one or more treatment options for the subject, to identify a treatment predicted to be effective for the subject, and/or to assign subjects into an appropriate arm within a clinical trial. In some embodiments, the output generating module 316 may output an indication of whether the subject is eligible for a clinical trial in testing a medical treatment for a particular medical condition based on the assessment 180.

The output from the digital pathology image processing system 310 can be provided in a number of forms, including a simple recitation of tire evaluations made by the digital pathology image processing system. More advanced output can also be provided. As an example, the digital pathology image processing system 310 can generate different visualizations of the identified histologies discussed herein. For example, the digital pathology image processing system 310 can generate an overall map depicting the various histologies, as shown in FIG. 4A. As another example, the digital pathology image processing system 310 can generate a separate map for each histology, as shown in FIG. 4B.

FIGS. 2A-2H illustrate another example processes 200 and 250 for identifying features a digital pathology image using a machine-learning model and generating a subject assessment based on heterogeneity of the features in the digital pathology image, respectively. Specifically, FIGS. 2A-2B illustrate identifying features, e.g., gene mutations or variants from patches of an example digital pathology image using a deep-learning neural network and evaluating heterogeneity of the identified mutations for diagnosing a condition in a subject or patient. FIG. 3 illustrates a network 300 of interacting computer systems that can be used, according to some embodiments described herein, for identifying gene mutations or variants from patches of an example digital pathology image using a deep-learning neural network and evaluating heterogeneity of the identified mutations. As mentioned earlier, pathologists cannot predict mutation status directly from H&E images and may instead rely on DNA sequencing, which is expensive and time-consuming. As such, using machine-learning techniques discussed herein to predict mutations or mutation status is significantly faster and more efficient than using DNA sequencing technique.

As illustrated in FIG. 2A, at 210, the digital pathology image processing system 310 receives a digital pathology image 205 of a tissue sample. In particular embodiments, the digital pathology image of the tissue sample can be a whole-slide image of a sample from a subject or patient diagnosed with non-small cell lung cancer. In a primary embodiment, the digital pathology image or the whole-slide image discussed herein is a H&E stained image or can be obtained from a H&E preparation of a tumor sample from the patient diagnosed with non-small cell lung cancer. The digital pathology image processing system 310 can receive the digital pathology image or the whole slide image 205 foam the digital pathology image generation system 320 or one or more components thereof. As another example, the digital pathology image processing system 310 can receive the digital pathology image 205 from one or more user devices 330. User device 330 can be a computer used by a pathologist or clinician connected via one or more networks to the digital pathology image processing system 310. The user of the user device 330 can use the user device 330 to upload the digital pathology image 205 or to direct one or more other devices to provide the digital pathology image 205 to the digital pathology image processing system 310.

In certain embodiments, although not shown in FIG. 2A, the digital pathology image processing system 310 may perform a tumor lesion segmentation on the image 210. For instance, a tumor region or area may be identified in the image 210. In one embodiment, the digital pathology image processing system 310 automatically identifies a tumor region using a separate tumor lesion segmentation algorithm or one or more machine-learning techniques. In one embodiment, the digital pathology image processing system 310 may identify a tumor region with the help of a user. For instance, the tumor region may be manually selected by a pathologist, a doctor, a clinical specialist, an expert in diagnosing lung cancers, etc. At 220, the digital pathology image processing system 310, for example using the patch generating module 311, subdivides the digital pathology image 205 (with identified tumor region) into a plurality of patches or tiles 215a, 215b, 215c, . . . 215n (also individually or collectively herein referred to as 215).

At 230, the digital pathology image processing system 310, for example using the patch classification module 312, identifies one or more image features within each of the patches and generates a plurality of labels 235a, 235b, 235c, . . . 235n (also individually or collectively herein referred to as 235) for the plurality of patches 215 corresponding to the identified image features using a deep-learning neural network 225. Each label 235 may indicate, identify, or predict a particular mutation type or gene variant. As an example, for patch 215a, the patch classification module 312 generates a corresponding label 235a indicating that one or more image features depicted in the patch 215a are associated with KRAS mutation, for patch 215b, the patch classification module 312 generates a corresponding label 235b indicating that one or more image features depicted in the patch 115b are associated with epidermal growth factor receptor (EGFR) mutation, for patch 115c, the patch classification module 312 generates a corresponding label 235c indicating that one or mom image features depicted in the patch 215b are associated with KRAS mutation, and for patch 215n, the patch classification module 312 generates a corresponding label 235n indicating that one or more image features depicted in the patch 215n are associated with EGFR mutation. Although only two types of labels or mutations KRAS and EGFR are illustrated in FIG. 2A, it should be noted that other types of mutations or gene variants may be similarly identified for patches using the deep-learning neural network 225.

FIG. 2B illustrates a process 250 for evaluating heterogeneity of the mutations identified in the digital pathology image (e.g., in the patches of the digital pathology image) for subject assessment based on the labels 235 generated through the process 200 in FIG. 2A, as discussed above. It should be noted that similar to FIG. 2A, references will be made to FIG. 3 for various computing components or modules that perform their respective operations in the process 250. As depicted, the digital pathology image processing system 310, for example using the image visualisation module 313, may feed the labelled patches (e.g., patches and the annotations indicating their depicted corresponding mutations) into an optional visualization tool or application 260. For instance, the image visualization module 313 may feed, along with the digital pathology image 205, a patch labeled KRAS 255a, a patch labeled EGFR 255b, a patch labelled KRAS 255c, a patch labelled EGFR 255n, and the remaining patches into the visualization tool 260. In some embodiments, the image visualization module 313 and the visualization tool 260 are combined or work together as a single component. In other embodiments, the image visualization module 313 and the visualization tool 260 are separate components.

At 265, the optional visualization tool 260 using the labelled patches 255 and the overall digital pathology image or whole slide image 205 can generate a patch-based signature 270 for the digital pathology image. It should be noted that the visualization tool 260 and patch-based signature 270 are shown with dotted lines to indicate that they are optional parts or components of the process 250 and may or may not be used in evaluating heterogeneity discussed herein. In particular embodiments, the patch-based signature or heatmap 270 may depict a visualization of the mutations within the tissue sample. The visualization may include displaying the predicted mutations or gene variants in different color codings. In particular embodiments, the digital pathology image processing system 310, for example using the image visualization module 313, may use different visualization techniques to generate the patch-based signature discussed herein. For instance, the image visualization module 313 may use one or more of a grad-cam technique, a score-cam technique, an occlusion mapping technique, or a saliency mapping technique to generate the visualization. Different visualization techniques are shown and discussed below in reference to FIG. 4C. In particular embodiments, the image visualization module 313 uses die saliency mapping technique to generate the patch-based signature 270.

At 275, the digital pathology image processing system 310, for example using the heterogeneity-metric computing module 314, computes a heterogeneity metric of the mutations identified in the digital pathology image (e.g., through the patches) using the labelled patches 255 (e.g., patches and their corresponding labels). The heterogeneity metric may include a quantifiable measure of the level or degree of heterogeneity of the mutations. In particular embodiments, the heterogeneity metric may quantify a relative proportion of each mutation with respect to other mutations in a given tissue sample. By way of an example, without limitation, the heterogeneity metric may indicate for KRAS and EGFR mutations identified in FIG. 2A, the percentage distribution of each of the KRAS and EGFR mutations in the tissue sample (e.g., non-small cell lung cancer image of the patient). The heterogeneity metric may indicate the existence of regions with different mutations in the same tumor. This is important because patients who received targeted therapy that is effective for tumors with certain mutations may not respond, or recur later, if there are some regions of the tumor that do not have that mutation.

The digital pathology image processing system 310, for example using the output generating module 316, generates an output based on the heterogeneity metric. In particular embodiments, the output can include a subject assessment 180 based on the computed heterogeneity metric. The subject assessment can include, for example, a subject diagnosis, subject prognosis, or treatment recommendation as applicable for the particular use case of the operator. For instance, based on the heterogeneity metric indicating how heterogenous the various features (e.g., mutations) are in a given tissue sample, the output generating module 316 may generate an appropriate assessment of the given tissue sample. As an example, the assessment may include an appropriate treatment option for Jang cancer in a patient based on the existence or heterogeneity of KRAS and EGFR gene mutations present in the tissue sample of the patient. In some embodiments, the output generating module 336 may provide the subject assessment 280 for display to a user, such as a pathologist, a doctor, a clinical specialist, an expert in diagnosing lung cancers, an operator of the digital pathology image processing system 310, etc. The subject assessment 280 can also be provided to one or more user devices 330. To some embodiments, the subject assessment 280 can be used to predict subject's responsiveness to various treatments, to identify a treatment predicted to be effective for the subject, and/or to assign subjects into an appropriate arm within a clinical trial. In some embodiments, the output generating module 316 may output an indication of whether the subject is eligible for a clinical trial in testing a medical treatment for a particular medical condition based on the assessment 280.

FIG. 3 illustrates a network 300 of interacting computer systems that can be used, as described herein, for identifying features in patches of a digital pathology image, generating labels for the identified features using deep-learning techniques, and generating an assessment basal on heterogeneity of the identified features in the digital pathology image according to some embodiments of the present disclosure.

A digital pathology image generation system 320 can generate one or more digital pathology images, including, but not limited to whole slide images, corresponding to a particular sample. For example, an image generated by digital pathology image generation system 320 can include a stained section of a biopsy sample or an unstained section of the biopsy sample to be presented for pre-processing. As another example, an image generated by digital pathology image generation system 320 can include a slide image (e.g., a blood film) of a liquid sample. As another example, an image generated by digital pathology image generation system 320 can include fluorescence microscopy such as a slide image depicting fluorescence in situ hybridization (FISH) after a fluorescent probe has been bound to a target DNA or RNA sequence.

Some types of samples can be processed by a sample preparation system 321 to fix and/or embed the sample. Sample preparation system 321 can facilitate infiltrating the sample with a fixating agent (e.g., liquid fixing agent, such as a formaldehyde solution) and/or embedding substance (e.g., a histological wax). For example, a sample fixation sub-system can fix a sample by exposing the sample to a fixating agent for at least a threshold amount of time (e.g., at least 3 hours, at least 6 hours, or at least 12 hours). A dehydration sub system can dehydrate the sample (e.g., by exposing the fixed sample and/or a portion of the fixed sample to one or more ethanol solutions) and potentially clear the dehydrated sample using a clearing intermediate agent (e.g., that includes ethanol and a histological wax). A sample embedding sub-system can infiltrate the sample (e.g., one or more times for corresponding predefined time periods) with a heated (e.g., and thus liquid) histological wax. The histological wax can include a paraffin wax and potentially one or more resins (e.g., styrene or polyethylene). The sample and wax can then be cooled, and the wax-infiltrated sample can then be blocked out.

A sample slicer 322 can receive the fixed and embedded sample and can produce a set of sections. Sample slicer 322 can expose the fixed and embedded sample to cool or cold temperatures. Sample slicer 322 can then cut the chilled sample (or a trimmed version thereof) to produce a set of sections. Each section can have a thickness that is (for example) less than 100 μm, less than 50 μm, less than 10 μm or less than 5 μm. Each section can have a thickness that is (for example) greater than 0.1 μm, greater than 1 μm, greater than 2 μm or greater than 4 μm. The cutting of the chilled sample can be performed in a warm water both (e.g., at a temperature of at least 30° C. at least 35° C. or at least 40° C.).

An automated staining system 323 can facilitate staining one or more of the sample sections by exposing each section to one or more staining agents. Each section can be exposed to a predefined volume of staining agent for a predefined period of time. In some instances, a single section is concurrently or sequentially exposed to multiple staining agents.

Each of one or more stained sections can be presented to an image scanner 324, which can capture a digital image of the section. Image scanner 324 can include a microscope camera. The image scanner 324 can capture the digital image at multiple levels of magnification (e.g., using a 10× objective, 20× objective, 40× objective, etc.). Manipulation of the image can be used to capture a selected portion of the sample at the desired range of magnifications. Image scanner 324 can further capture annotations and/or morphometries identified by a human operator. In some instances, a section is returned to automated staining system 323 after one or more images are captured, such that the section can be washed, exposed to one or more other stains and imaged again. When multiple stains are used, the stains can be selected to have different color profiles, such that a first region of an image corresponding to a first section portion that absorbed a large amount of a first slain can be distinguished from a second region of the image (or a different image) corresponding to a second section portion that absorbed a large amount of a second stain.

It will be appreciated that one or more components of digital pathology image generation system 320 can, in some instances, operate in connection with human operators. For example, human operators can move the sample across various sub-systems (e.g., of sample preparation system 321 or of digital pathology image generation system 320) and/or initiate or terminate operation of one or more sub-systems, systems or components of digital pathology image generation system 320. As another example, part or all of one or more components of digital pathology image generation system (e.g., one or more subsystems of the sample preparation system 321) can be partly or entirely replaced with actions of a human operator.

Further, it will be appreciated that, while various described and depicted functions and components of digital pathology image generation system 320 pertain to processing of a solid and/or biopsy sample, other embodiments can relate to a liquid sample (e.g., a blood sample). For example, digital pathology image generation system 320 can receive a liquid-sample (e.g., blood or urine) slide, that includes a base slide, smeared liquid sample and cover. Image scanner 324 can then capture an image of the sample slide. Further embodiments of the digital pathology image generation system 320 can relate to capturing images of samples using advancing imaging techniques, such as FISH, described herein. For example, once a florescent probe has been introduced to a sample and allowed to bind to a target sequence appropriate imaging can be used to capture images of the sample for further analysis.

A given sample can be associated with one or more users (e.g., one or more physicians, laboratory technicians and/or medical providers) during processing and imaging. An associated user can include, by way of example and not of limitation, a person who ordered a test or biopsy that produced a sample being imaged, a person with permission to receive results of a test or biopsy, or a person who conducted analysis of the test or biopsy sample, among others. For example, a user can correspond to a physician, a pathologist, a clinician, or a subject. A user can use one or one user devices 330 to submit one or more requests (e.g., that identify a subject) that a sample be processed by digital pathology image generation system 320 and that a resulting image be processed by a digital pathology image processing system 310.

Digital pathology image generation system 320 can transmit an image produced by image scanner 324 back to user device 330. User device 330 then communicates with the digital pathology image processing system 310 to initiate automated processing of the image. In particular embodiments, the image so produced after processing by one or more of the sample preparation system 321, the sample slicer 322, the automated staining system 323, or the image scanner 324 can be H&E stained imaged or an image produced through a similar staining procedure. In some instances, digital pathology image generation system 320 provides an image (e.g., H&E stained image) produced by image scanner 324 to the digital pathology image processing system 310 directly, e.g. at the direction of the user of a user device 330. Although not illustrated, other intermediary devices (e.g., data stores of a server connected to the digital pathology image generation system 320 or digital pathology image processing system 310) can also be used. Additionally, for the sake of simplicity only one digital pathology image processing system 310, image generating system 320, and user device 330 is illustrated in the network 300. This disclosure anticipates the use of one or more of each type of system and component thereof without necessarily deviating from the teachings of this disclosure.

The network 300 and associated systems shown in FIG. 3 can be used in a variety of contexts where scanning and evaluation of digital pathology images, such as whole slide images, are an essential component of the work. As an example, the net work 300 can be associated with a clinical environment, where a user is evaluating the sample for possible diagnostic purposes. The user can review the image using the user device 330 prior to providing the image to the digital pathology image processing system 310. The user can provide additional information to the digital pathology image processing system 310 that can be used to guide or direct the analysis of the image by the digital pathology image processing system 310. For example, the user can provide a prospective diagnosis or preliminary assessment of features within the scan. The user can also provide additional context, such as the type of tissue being reviewed. As another example, the network 300 can be associated with a laboratory environment were tissues are being examined, for example, to determine the efficacy or potential side effects of a drug. In this context, if can be commonplace for multiple types of tissues to be submitted for review to determine the effects on the whole body of said drug. This can present a particular challenge to human scan reviewers, who may need to determine the various contexts of the images, which can be highly dependent on the type of tissue being imaged. These contexts can optionally be provided to the digital pathology image processing system 310.

Digital pathology image processing system 310 can process digital pathology images, including whole slide images or H&E stained images, to classify features in the digital pathology images and generate labels/annotations for the classified features in the digital pathology images and related output, as discussed for example in reference to FIGS. 1A-1B and 2A-2B above. A patch generating module 311 can define a set of patches for each digital pathology image. To define the set of patches, the patch generating module 311 can subdivide the digital pathology image into the set of patches. As embodied herein, the patches can be non-overlapping (e.g., each patch includes pixels of the image not included in any other patch) or overlapping (e.g., each patch includes some portion of pixels of the image that are included in at least one other patch). Features such as whether or not patches overlap, in addition to the size of each patch and the stride of the window (e.g., the image distance or pixels between a patch and a subsequent patch) can increase or decrease the data set for analysts, with more patches (e.g., through overlapping or smaller patches) increasing the potential resolution of eventual output and visualizations and lead to a larger and more diverse dataset for training purposes. In some instances, patch generating module 311 defines a set of patches for an image where each patch is of a predefined size and/or an offset between patches is predefined. Furthermore, the patch generating module 311 can create multiple sets of patches of varying size, overlap, step size, etc., for each image. In some embodiments, the digital pathology image itself can contain patch overlap, which may result from the imaging technique. Even segmentation without patch overlapping can be a preferable solution to balance patch processing requirements. A patch size or patch offset can be determined, for example, by calculating one or more performance metrics (e.g., precision, recall, accuracy, and/or error) for each size/offset and by selecting a patch size and/or offset associated with one or more performance metrics above a predetermined threshold and/or associated with one or more optimal (e.g., high precision, highest recall, highest accuracy, and/or lowest error) performance metric(s). The patch generating module 311 may further define a patch size depending on the type of condition being detected. For example, the patch generating module 311 can be configured with awareness of the type(s) of histologies or mutations that the digital pathology image processing system 310 will be searching for and can customize the patch size according to the histologies or mutations to optimize detection, in some instances, patch generating module 311 defines a set of patches where a number of patches in the set, size of the patches of the set, resolution of the patches for the set, or other related properties, for each image is defined and held constant for each of one or more images.

In some embodiments, the patch generating module 311 can further define the set of patches for each digital pathology image along one or more color channels or color combinations. As an example, digital pathology images received by digital pathology image processing system 310 can include large-formal multi-color channel images having pixel color values for each pixel of the image specified for one of several color channels. Example color specifications or color spaces that can be used include the RGB, CMYK, HSL, HSV, or MSB color specifications. The set of patches can be defined based on subdividing the color channels and/or generating a brightness map or greyscale equivalent of each patch. For example, for each portion of an image, the patch generating module 311 can provide a red tile, blue tile, green tile, and/or brightness tile, or the equivalent for the color specification used. As explained herein, subdividing the digital pathology images bused on portions of the image and/or color values of the portions can improve the accuracy and recognition rates of the networks used to generating labels for the patches and image and to produce classifications of the image. Additionally, the digital pathology image processing system 310. e.g., using patch generating module 311, can convert between color specifications and/or prepare copies of the patches using multiple color specifications. Color specification conversions can be selected based on a desired type of image augmentation (e.g., accentuating or boosting particular color channels, saturation levels, brightness levels, etc.). Color specification conversions can also be selected to improve compatibility between digital pathology image generation systems 320 and the digital pathology image processing system 310. For example, a particular image scanning component can provide output in the HSL color specification and the models used in the digital pathology image processing system 310, as described herein, can be trained using RGB images. Converting the patches to the compatible color specification can ensure the patches can still be analyzed. Additionally, the digital pathology image processing system can up-sample or down sample images that are provided in particular color depth (e.g., 8-bit, 16-bit, etc.) to be usable by the digital pathology image processing system 310. Furthermore, the digital pathology image processing system 310 can cause patches to be converted according to the type of image that has been captured (e.g., fluorescent images may include greater detail on color intensity or a wider range of colors).

As described herein, a patch classification module 312 can identify or classify image features in patches of a digital pathology image and generate labels for these features. In some embodiments, classifying image features (e.g., features in a digital pathology image) may include classifying or identifying underlying tissue structures within a tissue sample. The patch classification module 312 can receive a set of patches from the patch generating module 311, identify one or more features in each of the patches, and generate one or more labels for these features using a machine-learning model. Each label may indicate a particular type of condition (e.g., histology subtype, mutation type) shown in the tissue sample. As an example, the digital pathology image may be an image of a sample from a patient diagnosed with non-small lung cancer type and the features identified by the patch classification module 312 may include different histologies, such as adenocarcinoma (ADC), squamous cell carcinoma (SCC), etc., as shown for example in FIG. 1A. As another example, the features identified by the patch classification module 312 may include different mutations or gene variants, such as KRAS mutation, epidermal growth factor receptor (EGFR) mutation, anaplastic lymphoma kinase (ALK) mutation, or tumor protein 53 (TP53) mutation, etc., as shown for example in FIG. 2A. In particular embodiments, the patch classification module 312 may identify the image features and generate corresponding labels to apply to the patches using a trained machine-learning model, such as deep-learning neural network 125 or 225 discussed herein. The model may be trained by a training controller 317 based on a process described below in reference to FIGS. 5A-5B or through a method discussed in FIG. 8.

As described herein, an image visualization module 313 can generate visualizations for analyzing digital pathology images. In particular embodiments, the image visualization module 313 may generate a visualization for a given digital pathology image based on features identified in live image, labels corresponding to tissue structure features and generated for the patches of the digital pathology image, and other related information. For instance, the image visualization module 313 may receive the labels or labelled patches from the patch classification module 312 and generate a visualization based on the labelled patches, as discussed for example in FIGS. 1B and 2B. In particular embodiments, one or more visualizations, such as visualizations shown in FIGS. 4A-4B, can be used by the pathologists to evaluate the machine-learning model discussed herein. For instance, a pathologist may review a visualization (e.g., heatmap) depicting various identified features and corresponding labels to assess whether the model correctly identifies these features and labels. Additionally or alternatively, the one or more visualizations can assist the pathologists in their diagnosis or assessment of the patient or review of an initial assessment.

In particular embodiments, a visualization generated by the image visualization module 313, is a patch-based signature, such as a heatmap, that characterizes the details of the identified features for review and/or analysis, it should be noted that heatmap is just one type of patch-based signature, and other types of patch-based signatures can also be generated and used for visualization discussed herein, in some embodiments, the digital pathology image processing system 310 can learn the patch-based signature and can use its learning in other predictions. This can include, for example, visualization of raw count numbers, percentages of labeled patches, percentage of labeled patches relative to the rest of the slide/tumor area, statistical distribution of the labeled patches, spatial distribution of the patches, etc.

Figure 4D:
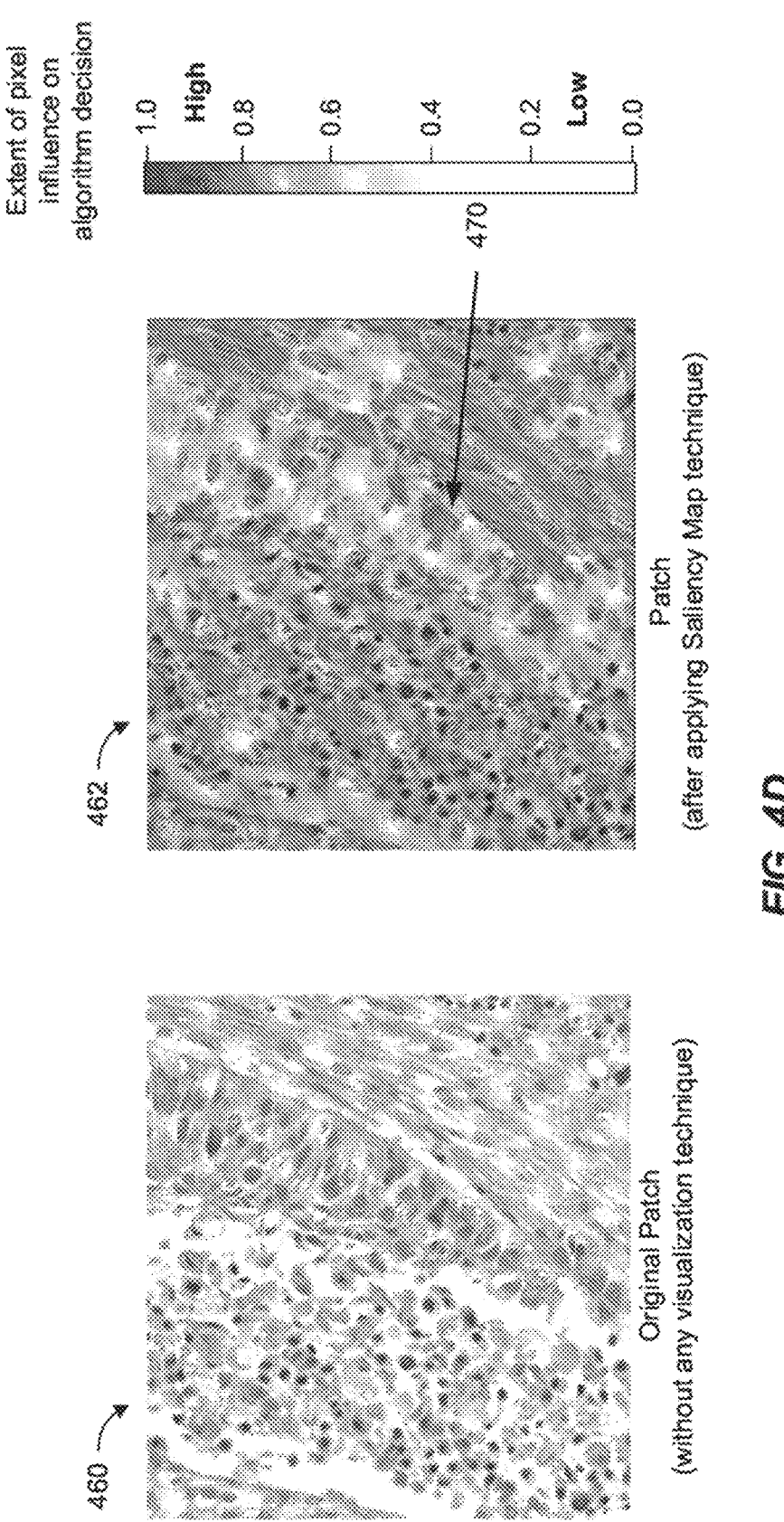
FIG. 4D illustrates an example of visualizing an image with a saliency mapping technique.

The patch-based signature may depict a visualization of the identified features in the tissue sample. For instance, the visualization may include displaying the features (e.g., histologies, imitations) in different color codings, as described elsewhere herein. In particular embodiments, the image visualization module 313 may use different visualization techniques to generate its visualization (e.g., patch-based signature). For instance, the image visualization module 313 may use one or more of a gradient-weighted class activated mapping (Grad-CAM) technique, a score-weighted class activated mapping (score-CAM) technique, an occlusion mapping technique, and a salience mapping technique to generate the visualization, as shown and discussed for example in FIG. 4C. In one embodiment, the image visualization module 313 may select the saliency mapping technique as its preferred and desired technique for visualizing the various features in an image. FIG. 4D illustrates an example of visualizing an image with the selected saliency mapping technique.

As described herein, a heterogeneity-metric computing module 314 can compute a heterogeneity metric based on features and/or labels identified in a digital pathology image. The heterogeneity metric may include a quantifiable measure of the level or degree of heterogeneity of the features including histologies, mutations, etc. based on the labels (e.g., histology subtypes, mutation types) corresponding to these features, in particular embodiments, the heterogeneity metric may indicate, using the labels, a relative proportion of each feature in tissue structures with respect to other features in the tissue structures. As an example, the heterogeneity metric can include, raw count numbers of the labels, percentages of labeled patches, percentages of labeled patches relative to the rest of the slide and/or tumor area, a statistical distribution of the labeled patches, a spatial distribution of the labeled patches, and other related metrics and derivations thereof.

By way of an example, without limitation, the heterogeneity metric may indicate for the various histologies identified in FIG. 1A, the percentage of each of the ADC and SCC subtype of lung cancer in the tissue sample (e.g., non-small cell lung cancer histology image of the patient). Stated differently, the heterogeneity metric may indicate how many total ADC cancer regions are present with respect to the total SCC cancer regions in the tissue sample, as shown in FIG. 1B. As another example, the heterogeneity metric may indicate for the various mutations or gene variants identified in FIG. 2A, the percentage of each of the KRAS and EGFR mutations in a given tissue sample of a subject or patient. The heterogeneity metric may be used to diagnose a particular condition in a patient. For example, the heterogeneity metric may be used to diagnose heterogeneity in the patient based on an amount of ADC and SCC cancer regions present in a tissue sample of the patient.

An output generating module 316 of the digital pathology image processing system 310 can use the digital pathology image, image classifications (e.g., labelled patches), image visualizations (e.g., patch-based signature), and heterogeneity-metric(s) to generate output corresponding to the digital pathology image received as input. As described herein, in addition to labels and annotations for the digital pathology image, the output can include a variety of visualizations and diagnosis corresponding to these visualizations. The output can further include a subject assessment based on the tissue sample. As an example, the output for a given digital pathology image can include a so-called heatmap that identifies and highlights areas of interest within the digital pathology image, as shown for example in FIGS. 4A-48. A heatmap can indicate portions of an image that depict or correlate to a particular condition or diagnosis and may indicate the accuracy or statistical confidence of such indication(s). In many embodiments, the output will be provided to the user device 330 for display, but in certain embodiments the output can be accessed directly from the digital pathology image processing system 310.

A training controller 317 of the digital pathology image processing system 310 can control training of the one or more machine-learning models discussed herein (e.g., deep-learning neural networks) and/or functions used by digital pathology image processing system 310. In some instances, one or more of the neural networks used by digital pathology image processing system 310 used to identify or detect features (e.g., histologies, mutations, etc.) within tissue samples are trained together by the training controller 317. In some instances, the training controller 317 can selectively train the model for use by the digital pathology image processing system 310. For example, the digital pathology image processing system 210 can use a First training technique to train a first model for feature classification in digital pathology images, a second training technique to train a second model for computing heterogeneity metric, and a third training technique to train a third model for identifying tumor areas or regions in the digital pathology images. The training of a machine-learning model (e.g., deep-learning neural network) is described in detail below in reference to at least processes 500 and 550 of FIG. 5A 5B and method 800 of FIG. 8.

FIG. 4A illustrates example visualizations that may be generated based on image features and corresponding labels identified using the machine-learning model discussed herein. In particular, FIG. 4A illustrates an example heatmap 400 and a detailed view 410 of the same heatmap 400. The heatmap may be comprised of multiple cells. In particular embodiments, the heatmap may be one example of a patch-based signature. The cells of the heatmap can correspond directly to the patches generated from the digital pathology image, as discussed above in reference to at least FIGS. 1A-1B and 2A-2B. Each cell may be assigned an intensity value, which can be normalized across all of the cells (e.g., such that the intensity values of the cells range from 0 to 1, 0 to 100, etc.). In displaying the heatmap 400, the intensity values of the cells can be translated to different colors, patterns, intensities, etc. In the example shown in FIG. 4A, 402 represents a tumor region or area and within the tumor region 402, dark grey regions 404a, 404b, 404c, 404d, and 404c (also individually and collectively referred to herein as 404) represent ADC cancer regions, while the light grey cells 406a, 406b, 406c, and 406d (also individually and collectively referred to herein as 406) represent SCC cancer regions. Although not shown, different mutations (e.g., KRAS mutation, EGFR mutation, etc.) may be similarly visualized using the heatmap discussed herein. Color gradients can be used to illustrate the different histologies or mutations, as identified using the processes discussed in FIGS. 1A-1B and 2A-2B. In particular embodiments, the intensity values of each cell can be derived from the labels determined for the corresponding patch by the deep-learning neural network discussed herein. Thus, the heatmap can be used to quickly identify patches of the digital pathology image that the digital pathology image processing system 310, and the patch classification module 312 in particular, have identified as likely including indicators of a specific condition, such as a particular histology, a particular gene mutation, a particular gene variant, etc. in particular embodiments, the visualizations 400 and 410 depicted in FIG. 4A are generated using one or more of the visualization tool 160, the visualization tool 260, the image visualization module 313, or the output generating module 316.

FIG. 4B illustrates other example visualizations that may be generated based on image features and corresponding labels identified using the machine-learning model discussed herein. In particular, FIG. 4B shows an example where two heatmaps 420 and 430 may be produced for a single digital pathology image. Each heatmap 420 or 430 depicts visualizations relating to a single label that is indicative of a specific feature. For instance, rather than a single heatmap depicting visualizations of two or more features, such as the heatmap 400, a separate heatmap may be generated corresponding to each feature, where each heatmap for a particular feature shows regions of that feature within the map. As illustrated, the heatmap 420 illustrates regions 422a, 422b, 422c, and 422d of SCC, while the heatmap 430 illustrates regions 432a, 432b, and 432c of ADC. In a similar manner, separate heatmaps may be generated for visualizing each of the mutations or gene variants.

FIG. 4C illustrates visualizing an example digital pathology image using the various visualization techniques. These visualization techniques include a gradient-weighted class activated mapping (Grad-CAM) technique, a score-weighted class activated mapping (score-CAM) technique, an occlusion mapping technique, and a saliency mapping technique. In particular embodiments, the image visualization module 313 of the digital pathology image processing system 310 is capable of using each of these different visualization techniques to generate various patch-based signatures.

As illustrated, image 450 shows an original patch before applying a visualization technique. Image 452 shows the patch after applying a Grad-CAM technique. The Grad CAM technique uses the gradients of any target concept, flowing into the final convolutional layer of a convolutional neural network (CNN) to produce a coarse localization map highlighting important regions in the image for predicting the concept. Next, image 454 shows the patch after applying a Score-CAM technique. The Score-CAM technique is a gradient-free visualization method, extended from Grad-CAM and Grad-CAM++. It achieves better visual performance and fairness for interpreting the decision-making process. Next, image 456 shows the patch after applying an occlusion mapping technique. The occlusion mapping technique is a shadowing technique that is used to make 3D objects look more realistic by simulating soft shows that should naturally occur when indirect or ambient lighting is cast out onto the image. In some embodiments, an occlusion map is a greyscale image, with white indicating areas that should receive full indirect light, and black indicating no indirect lighting. Next, image 458 shows the patch after applying a saliency mapping technique. The saliency mapping technique is a technique that uses saliency to identify unique features (pixels, resolution, etc.) in an image. The unique features depict important or relevant locations in art image. In particular embodiments, the saliency mapping technique identifies regions in an image that the machine-learning model (e.g., deep-learning neural network) uses to make its label predictions. In particular embodiments, a saliency map is also a heat map where hotness refers to those regions of the image which have a big impact on predicting a class which an object belongs to. The purpose of the saliency map is to find regions which are prominent or noticeable at every location in the visual field and to guide the selection of attended locations based on the spatial distribution of saliency.

Based on comparing the different visualization techniques and the results obtained based on these techniques, as discussed above in reference above to FIG. 4C, the image visualization module 313 may select a preferred technique for visualizing the various features (e.g., mutations) in an image. Additionally, a user operator of die image visualization module 313 can specify the desired technique. As an example, based on analyzing or examining the patches 450, 452, 454, 456, and 458 obtained after applying the different visualization techniques in FIG. 4C, the image visualization module 313 may determine the results of the saliency map as most accurate and clear in depicting the features (e.g., ADC, SCC) in the image. FIG. 4D illustrates an example of visualizing an example digital pathology image with the selected saliency mapping technique. Similar to FIG. 4C, 460 shows an original SCC patch before applying any visualization technique and 462 shows resulting SCC patch after applying the saliency mapping technique discussed herein. The application of the saliency mapping technique helps to show area of the tissue that had the most impact in a decision by a deep-learning neural network to make a prediction about a label. As indicated by reference numeral 470, the saliency map has picked out cell nuclei in the SCC patch without a segmentation algorithm.

Figure 5A:
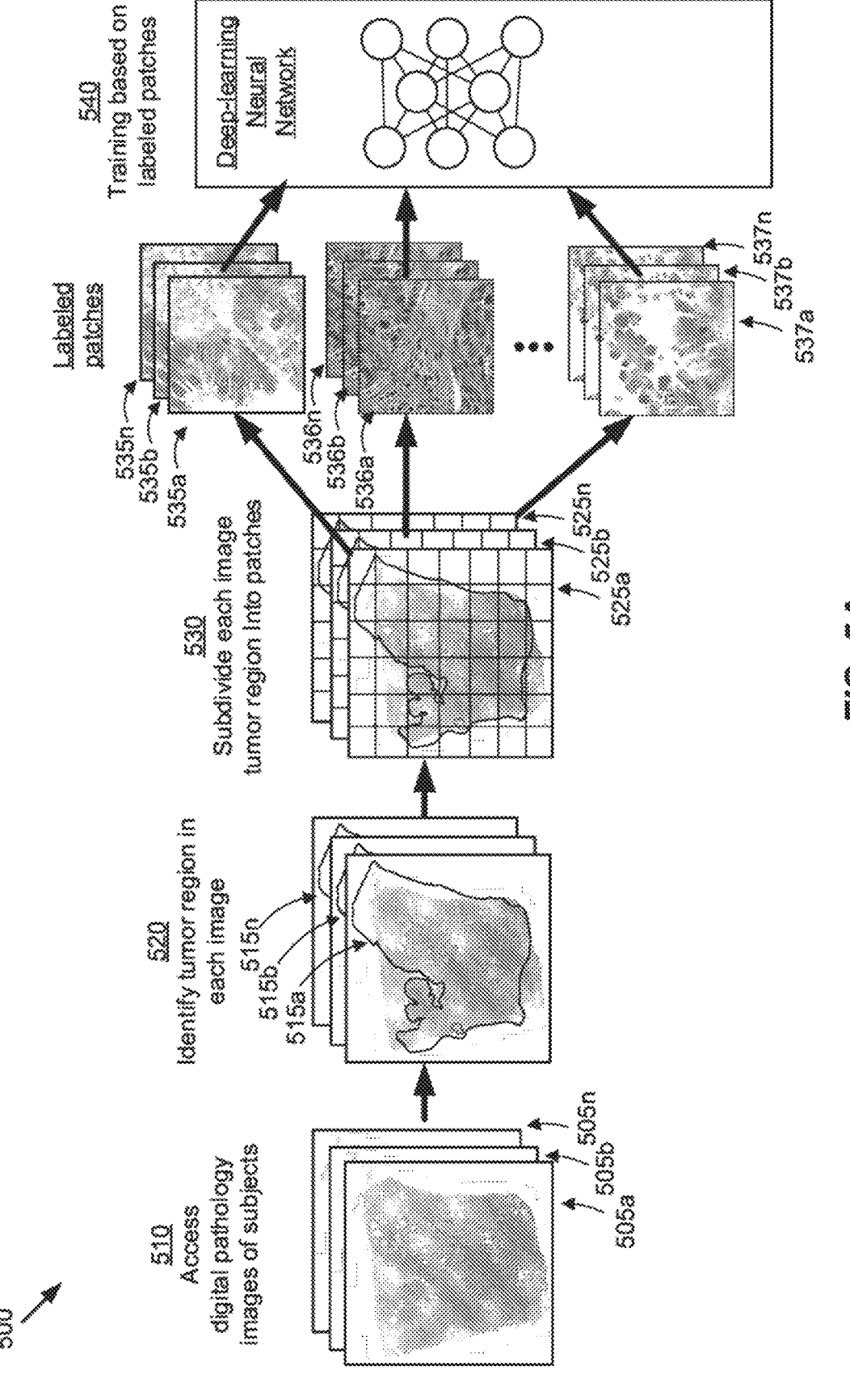
FIGS. 5A-5B illustrate an example embodiment of training a machine-learning model for classifying patches of digital pathology images according to detection of image features depicted in the patches.
Figure 5B:
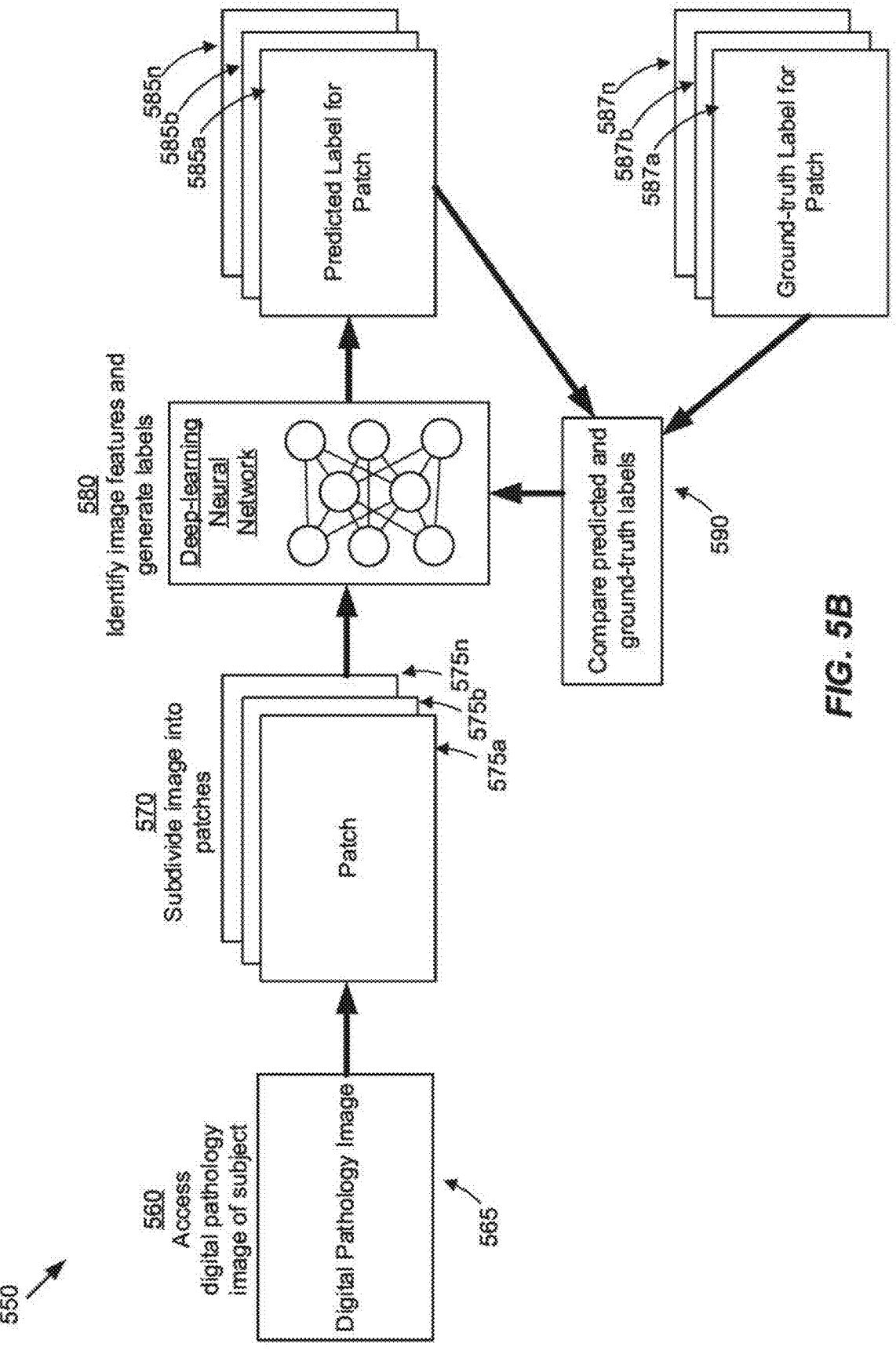

FIGS. 5A-5B illustrate example processes 500 and 550 for training a machine-learning model for classifying digital pathology images according to detection of image features depicted in the patches and testing and updating the machine-learning model, respectively. FIG. 5A illustrates an example process 500 for training the digital pathology image processing system 310 and in particular for training the deep-learning neural network used for identifying features (e.g., histologies, mutations, etc.) within tissue samples. In general, the training process involves providing training data (e.g., digital pathology images or whole slide images of various subjects) with ground truth features and corresponding labels to the digital pathology image processing system 310, causing the deep-learning neural network to learn to identify various features (e.g., histologies, mutations, etc.) and generate corresponding labels in a given digital pathology or whole slide image. The ground truth labels used for training may be provided by clinicians/pathologists and may include diagnosis of the tumor type such as histology subtype including, for example, adenocarcinoma and squamous cell carcinoma, and DMA sequencing for mutations. The training is particularly advantageous as it reduces the burden on users (e.g., pathologists, doctors, clinical specialist, etc.) in manually evaluating thousands of whole slide images and identifying features in each of these images. Using a trained machine-teaming model to identify histologies or mutations within tissue samples expedites the overall image classification and evaluation process. Once the model is sufficiently trained, model can reduce the number of errors or chances for errors that can be introduced in manual classification and evaluation by humans. As an example, the trained model may be able to automatically identify different mutations or gene variants, which were difficult or not possible to be predicted by humans manually from images alone. Also, the trained machine-learning model sometimes helps to identify novel biomarkers or features that were previously unknown.

In some embodiments, the model for this type of learning structure can be referred to as multiple instance learning. In multiple instance learning, a collection of instances are provided together as a set with a label. Note that the individual instances are often not labelled, just the set. The label is typically based on a condition being present. The basic assumption in the multiple instance learning techniques employed by the system described is that when a set of patches is labelled as having the condition present (e.g., when a set of patches is labelled as being associated with a particular mutation type) then at least one instance in the set is of the particular mutation type. Similarly, when the set of patches is labelled as being associated with a particular histology, then at least one instance in the set is of the particular histology. In other embodiments, patches may be individually labelled and a set of patches may contain individually labelled patches, where a label associated with one patch in the set is different from a label associated with another patch in the set.

As described herein, a training controller 317 of the digital pathology image processing system 310 can control training of the one or more machine-learning models discussed herein (e.g., deep learning neural networks) and/or functions used by digital pathology image processing system 310 for identifying features (e.g., histologies, mutations, etc.) within tissue samples. As illustrated in FIG. 5A, at 510 the training controller 317 can select, retrieve, and/or access training data that includes a set of digital pathology image, (e.g., whole slide images 505a, 505b, . . . , 505n). Although three images are depicted in FIG. 5A as being part of the training data, it should be noted that this is not by any way limiting and any number of images may be used in the training. For example, 1000 digital pathology images including tissue samples from NSCLC patients may be used for training the machine learning model (e.g., deep-learning neural network) discussed herein.

At 520 the training controller 317 may perform tumor lesion segmentation e.g., identify a tumor region (e.g., disease area) in each of the digital pathology images. For example, as illustrated in FIG. 5A, a tumor region 515a is identified in image 505a, a tumor region 515b is identified in image 505b, and a tumor region 515n is identified in image 505n. In one embodiment, the training controller 317 automatically identifies a tumor region using one or more machine-learning techniques. For instance, a machine-teaming model may be trained based on pre-labeled or pre-annotated tumor regions in a set of digital pathology images by human experts. In some embodiments, the training controller 317 may identify a tumor region with the help of a user. For instance, the tumor region may be manually selected by a pathologist, a doctor, a clinical specialist, an expert in diagnosing lung cancers, etc.

At 530 the training controller 317 causes the digital pathology image processing system 310, for example using a patch generating module 311, to subdivide each digital pathology image with identified tumor region into a set of patches or tiles. For example, as illustrated in FIG. 5A, image 525a is subdivided into a set of patches 535a, 535b, . . . , 535n (also individually and collectively herein referred to as 535), image 525b is subdivided into a set of patches 536a, 536b, . . . , 536n (also individually and collectively herein referred to as 536), and image 525n is subdivided into a set of patches 537a, 537b, . . . , 537n (also individually and collectively herein referred to as 537). Each patch in the sets 535, 536, and 537 may be classified with one or more image features and annotated with corresponding labels for these features. For instance, one or more human experts or pathologists may annotate each patch with a label identifying or indicative of a certain feature within a tissue sample. By way of an example, without limitation, pathologists may classify or identify one or more features in each patch and provide a label for each of the identified features, where the label is indicative of a particular histology, such as ADC or SCC, within a tissue sample. By way of another example, without limitation, a label indicating a particular mutation or gene variant, such as KRAS ALK, TP53, within a tissue sample may be provided by the pathologists for each of the patches. This process may be repealed until all the extracted patches are classified, annotated, or labeled. In certain embodiments, a single ground truth label for a patient may be used to label each patch (that belongs to the tumor lesion) of an image of a sample from the patient. In reality, labels for patches may be different are not the same, and therefore, the training is weakly supervised learning.

It should be understood that the training process 500 illustrated in FIG. 5A is not limited to the order or arrangement of the steps 510, 520, 530, and 540 as shown in FIG. 5A and rearrangement of one or more steps of the training process 500 is possible and within the scope, of the present disclosure. For instance, in one embodiment, the subdividing or tiling step 530 can occur before tumor lesion segmentation step 520. In this embodiment, the digital pathology images 505a, 505b, . . . 505n of the subjects are first subdivided into a plurality of patches, and them tumor lesion segmentation is performed on each of these patches (e.g., tumor region is identified in each of the patches) using either manual annotations, or a separate tumor segmentation algorithm. In another embodiment the training process 500 is performed in the order as illustrated in FIG. 5A. Other variations and one or more additional steps in the training process 500 are also possible and contemplated.

At step 540 the training controller 317 may train a machine-learning model (e.g., deep-learning neural network) based on the labeled set of patches 535, 536, and 537. For instance, the training controller 317 may feed each labeled patch (e.g., patch with identified features) and corresponding label(s)) into the machine-learning model for training using CNN training approaches that will be understood by persons of skill in the art. Once trained, the machine-learning model may be able to classify tissue patches using whole-slide level labels, as discussed elsewhere herein.

FIG. 5B illustrates a process 550 for testing and updating the machine-learning model that is trained to identify and classify features in digital pathology images and/or patches segmented from digital pathology images using the process 500 of FIG. 5A. For instance, once the machine-learning model is trained based on the plurality of digital pathology images 505a, 505b, . . . , 505n and corresponding patch labels 535a, 535b, . . . , 535n, 536a, 536b, . . . , 536n, and 537a, 537b, . . . , 537n as discussed above in reference to FIG. 5A, the trained machine-learning model may be tested on one or more unseen test slides or digital pathology images to verify an accuracy of the trained machine-learning model in its classification. As an example, the trained machine-learning model may be made to perform its testing on 20 unseen test slides for the verification. The test slides or images for testing the machine-learning model may be any number and may be preset by a user. Based on the verification, a confidence in the model may be determined.

At 560 the training controller 317 may access a particular digital pathology image 565 of a particular subject for testing the trained machine learning model. At step 570, the digital image processing system 310 may subdivide the particular digital pathology image 565 into a plurality of patches 575a, 575b, . . . , 575n (individually and collectively herein referred to as 575). At 580 the training controller 317 identifies image features and generates labels for the image features identified in the plurality of patches 575 using the trained machine-learning model obtained through the process 500 of FIG. 5A. For instance, the training controller 317 generates a predicted label 585a for features) depicted in the patch 575a, a predicted label 585b for feature(s) depicted in the patch 575b, and a predicted label 585n for feature(s) depicted in the patch 575n.

At 590 the training controller 317 may access ground-truth labels or classifications for each of the patches 575a, 575b, . . . 575n. As illustrated, a ground-truth label 587a corresponds to the feature(s) depicted in patch 575a, a ground-truth label 587b corresponds to the feature(s) depicted in patch 575b, and a ground-truth label 587n corresponds to the feature(s) depicted in patch 575n. In particular embodiments, the ground-truth labels are labels or classifications that are known to be the accurate or ideal classification. For example, the ground-truth labels can be provided as part of the dataset of training images and can be generated by a pathologist or other human operator. Upon accessing the ground-truth labels, at step 590, the training controller 317 may compare the predicted labels 585a, 585b . . . 585n with corresponding ground-truth labels or true labels 587a, 587b, . . . , 587n. For instance, the training controller 317 compares the predicted label 585a with ground-truth label 587a, the predicted label 585b with ground-truth label 587b, and the predicted label 585n with ground-truth label 587n. In some embodiments, based on the comparison, the training controller 317 may compute a scoring function for the training process, such as a loss function. The scoring function (e.g. loss function) may quantify differences in classifications between the predicted labels by the deep-learning neural network, and the ground-truth labels. For instance, the loss function may indicate an offset value describing how off or far the predicted labels by the machine-learning model are from the ground-truth or true labels. A comparison of predicted labels with true labels is shown, for example, in FIG. 6.

Based on the comparison 590, the training controller 317 may determine whether to cease training or update the machine-learning model (e.g., deep-learning neural network). For instance, the training controller 317 can determine to train the deep-learning neural network until the loss function indicates that the deep-learning neural network has passed a threshold value of concordance between the predicted labels 585a, 585b, . . . , 585n and the ground-truth labels 587a, 587b, . . . , 587n. In some embodiments, the training controller 317 can determine to train the deep-learning neural network for a set number of iterations or epochs. For instance, the deep-learning neural network can be trained and updated using the same set of labelled patches 535, 536, and 537 repeatedly until a specified number of iterations has been reached or until some threshold criteria is met. The training controller 317 can also perform multiple iterations to train the deep-learning neural network using a variety of training images. The deep-learning neural network can also be validated using a reserved test set of images. In some embodiments, the training controller 317 can periodically pause training and provide a test set of patches where the appropriate label is known. The training controller 317 can evaluate the output of the deep-teaming neural network against the known labels on the test set to determine the accuracy of the deep-teaming neural network. Once the accuracy reaches a set threshold, the training controller 317 can cease training of the deep-learning neural network.

In some embodiments, once the training controller 317 determines that the training is complete, the training controller 317 may output a confidence value indicating a confidence or accuracy in classification of the trained machine-learning model (e.g., deep-learning neural network. For example, the training controller 317 may output a confidence value 0.95 indicating that the deep-learning neural network is 95% accurate in classifying the features in test images of subjects. Example confidence values indicating accuracy of the model is illustrated, for example in FIG. 6.

As described herein, the traditional process for identifying image features and generating corresponding labels for digital pathology images (e.g., whole slide images) is arduous and time-consuming. The digital pathology image processing system 310 and tire methods of use and training said system described herein can be used to increase the set of images available for training the various networks of the digital pathology image processing system. For example, after an initial training pass using data with known labels (including, potentially annotations), the digital pathology image processing system 310 can be used to classify patches without existing labels. The generated classifications can be verified by human agents and, should correction be needed, the digital pathology image processing system 310 (e.g., deep-learning neural network) can be retrained using the new data. This cycle can repeat, with the expectation that viewer interventions will be required to improve the accuracy rate on previously unseen examples. Additionally, once a specified level of accuracy has been reached, the labels generated by the digital pathology image processing system 310 can be used as a ground-truth for training.

Figure 6:
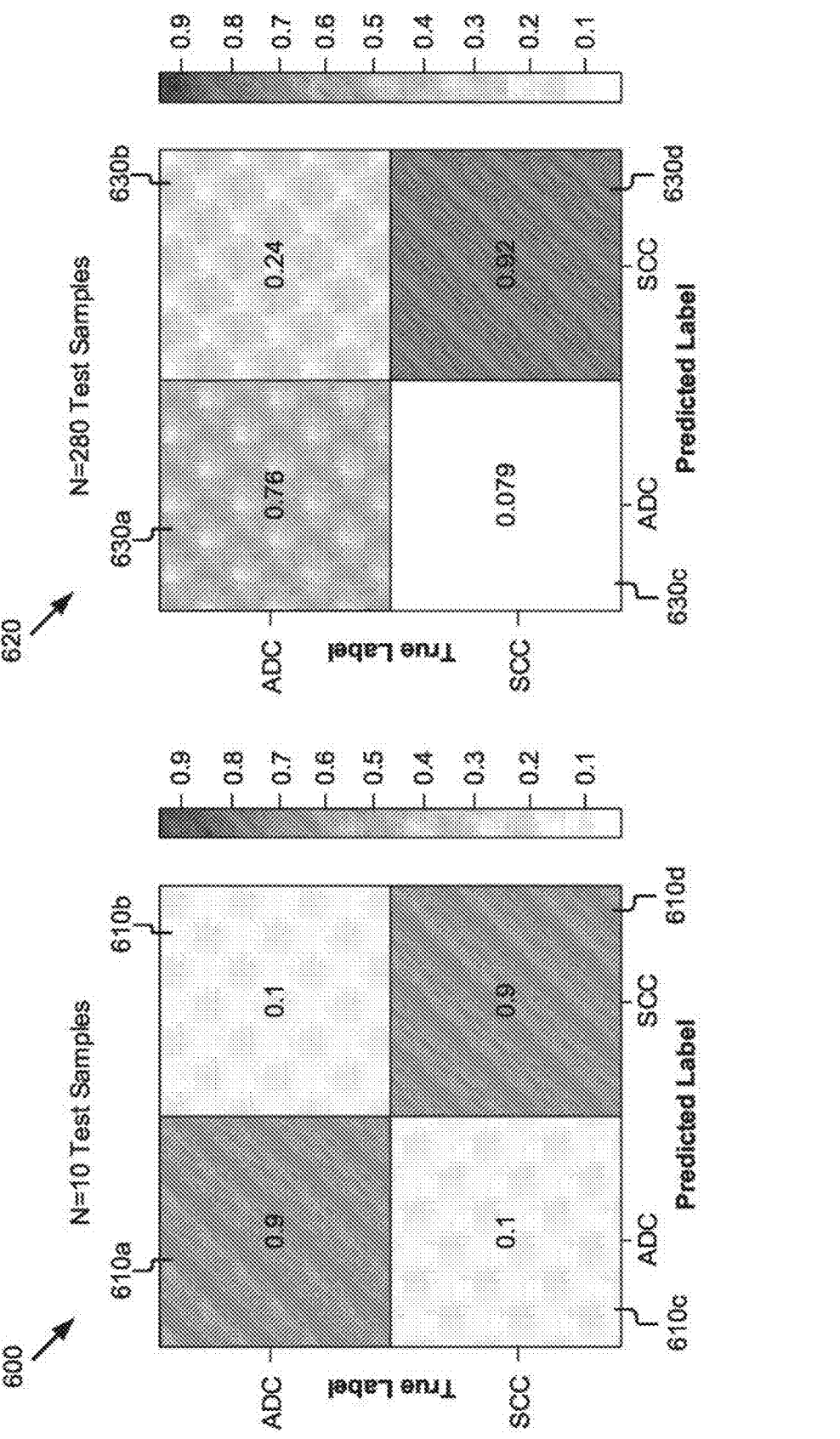
FIG. 6 illustrates example experimental comparison data between predicted labels and true labels based on two different sampling data.

FIG. 6 illustrates example experimental comparison data between predicted labels and true labels based on two different sampling data. In particular, FIG. 6 shows an accuracy of the machine-teaming model (e.g., deep-learning neural network) in predicting or identifying histologies, such as ADC and SCC, for two different numbers of test samples. A chart 600 on the left illustrates confidence values 610*a*, 610*b*, 610*c*, and 610*d* indicating an accuracy of the model in predicting or identifying the ADC and SCC regions based on 10 test samples. As depicted, the training controller 317 outputs a 0.9 confidence value (as indicated by reference numerals 610*a* and 610*d*) indicating (hat there is 90% concordance between the true labels and the predicted labels. Stated differently, the training controller 317 may find the trained model (e.g., deep-learning neural network) 90% accurate in correctly identifying the ADC and SCC regions within the 10 test samples.

A chart 620 on the right illustrates confidence values 630*a*, 630*b*, 630*c*, and 630*d* indicating an accuracy of the model in predicting or identifying the ADC and SCC regions based on 280 test samples. As depicted, the training controller 317 outputs a 0.76 confidence value (indicated by reference numerals 630*a*) in the model identifying ADC within these samples and a 0.92 confidence value (indicated by reference numeral 630*d*) in the model identifying SCC within these samples. Specifically, the confidence values 630*a* and 630*d* respectively indicates that there is 76% concordance between the true labels and predicted labels when identifying the ADC within these samples and 92% concordance when identifying the SCC within these 280 test samples.

FIG. 7 illustrates an example method 700 for identifying features in a digital pathology image using a machine-learning model and generating a subject assessment based on heterogeneity of the identified features in the digital pathology image. The method 700 can begin at step 710, where the digital pathology image processing system 310 receives or otherwise accesses a digital pathology image of a tissue sample. In particular embodiments, the digital pathology image of the tissue sample is a whole-slide image of a sample from a subject or patient diagnosed with non small cell lung cancer. In one embodiment, the digital pathology image or the whole-slide image discussed herein is a H&E stained image or can be obtained from a H&E preparation of a tumor sample from the patient diagnosed with non-small cell lung cancer. As described herein, the digital pathology image processing system 310 can receive the image from a digital pathology image generation system directly or can receive the image from a user device 330. In other embodiments, the digital pathology image processing system 310 can be communicatively coupled with a database or other system for storing digital pathology images that facilitates the digital pathology image processing system 310 receiving the image for analysis.

At step 715, the digital pathology image processing system 310 subdivide the image into patches. For example, the digital pathology image processing system 310 can subdivide the image into patches as shown in FIGS. 1A and 2A. As described herein, the digital pathology image is expected to be significantly larger than standard images, and much larger than would normally be feasible for standard image recognition and analysis (e.g., on the order of 100,000 pixels by 100,000 pixels). To facilitate analysis, the digital pathology image processing system 310 subdivides the image into patches. The size and shape of a patch is uniform for the purposes of analysts, but the size and shape can be variable. In some embodiments, the patches can overlap to increase the opportunity for image context to be properly analyzed by the digital pathology image processing system 310. To balance the work performed with accuracy, it may be preferable to use non-overlapping patches. Additionally, subdividing the image into patches can involve subdividing the image based on a color channel or dominant color associated with the image.

At step 720, the digital pathology image processing system 310 identifies and classifies one or more image features (e.g., histologies, mutations, etc.) in each of the patches and at step 825, generates one or more labels tor the one or more image features identified in each patch of the digital pathology image using a machine learning model, where each label may indicate a particular type of condition (e.g., cancer type, type of tumor cell, mutation type, etc.) in the tissue sample. In one embodiment, the digital pathology image is an image of a sample from a patient with non-small lung cancer type and the labels generated at step 825 by the machine-learning model may indicate histology subtypes, such as adenocarcinoma (ADC), squamous cell carcinoma (SCC), etc., as shown for example in FIG. 1A. In another embodiment, the labels generated at step 825 by the machine-learning model may indicate different mutations or gene variants, such as KRAS mutation, epidermal growth factor receptor (EGFR) mutation, anaplastic lymphoma kinase (ALK) mutation, or tumor protein 53 (TP53) mutation, etc., as shown for example in FIG. 2A. It should be understood that the machine-learning model discussed herein is not limited to generating labels corresponding to different histologies and mutations in a tissue sample, and labels corresponding to other variety of features in the tissue sample may also be generated by the machine-learning model. In particular embodiments, the machine-learning model discussed herein is a deep-learning neural network.

At step 730, the digital pathology image processing system 310 can optionally generate a patch-based signature based on the labels generated using the machine-learning model above. For example, the digital pathology image processing system 310 can generate a patch-based signature as shown in FIGS. 4A-4B. In particular embodiments, the patch-based signature is a heatmap that includes a plurality of regions associated with a plurality of intensity values, respectively. One or more regions of the plurality of regions of the heatmap may be associated with an indication of a condition in the patient sample, and a respective intensity value associated with the one or more regions correlates to a statistical confidence of the indication. The patch-based signature may depict a visualization of the identified features in the tissue sample. The visualization may include displaying the features (e.g., histologies, mutations) in different color codings. By way of an example, without limitation, visualizing different histologies in a tissue sample through a patch-based signature may include displaying ADC in blue color, SCC in green color, etc. In particular embodiments, the digital pathology image processing system 310 may use different visualization techniques to generate the patch-based signature (e.g., heatmap) discussed herein. For instance, the image visualization module 313 may use one or more of a Grad-CAM technique, a Score-CAM technique, an occlusion mapping technique, or a saliency mapping technique to generate the visualization, as shown and discussed for example in FIG. 4C. In one embodiment, the visualization technique used here is the saliency mapping technique, as shown and discussed for example in FIG. 4D.

At step 735, the digital pathology image processing system 310 computes a heterogeneity metric using live labels generated in step 725. In an alternative embodiment, the digital pathology image processing system 310 can compute a heterogeneity metric using the patch-based signature generated in step 730. In particular embodiments, the heterogeneity metric may indicate a relative proportion of each label in the tissue sample with respect to other labels within the tissue sample. By way of an example, without limitation, the heterogeneity metric may indicate for the various histologies identified in FIG. 1A, the percentage of each of the ADC and SCC cancer regions in the tissue sample (e.g., non-small cell lung cancer image of the patient). Stated differently, the heterogeneity metric may indicate how many total ADC cancer regions are present with respect to the total SCC cancer regions in the tissue sample, as shown in FIG. 1B. As another example, the heterogeneity metric may indicate for the various mutations or gene variants identified in FIG. 2A, the percentage of each of the KRAS and FGFR mutations in a given tissue sample of a subject or patient. As another example, the heterogeneity metric may provide a metric quantifying a degree or magnitude of heterogeneity or otherwise contribute to such a metric.

At step 740, the digital pathology image processing system 310 generates a subject assessment based on the computed heterogeneity or the heterogeneity metric. The subject assessment can include, as an example and not limitation, a subject diagnosis, prognosis, treatment recommendation, or other similar assessment based on the heterogeneity of the features in the digital pathology image. For instance, based on the heterogeneity metric indicating how heterogenous the various features (e.g., histologies or mutations) and their corresponding labels are in a given tissue sample, the output generating module 316 may generate an appropriate assessment of the given tissue sample. As an example, the assessment may include a severity of the lung cancer in a patient based on an amount of ADC and SCC cancer regions present in the tissue sample of the patient.

At step 745, the digital pathology image processing system 310 provides the generated subject assessment to a user, such as a pathologist, a doctor, a clinical specialist, an expert in diagnosing lung cancers, an operator of an imaging device, etc. In particular embodiments, the user can use the assessment generated in step 740 to assess treatment options for a patient. In some embodiments, the output generating module 316 may output an indication of whether the subject is eligible for a clinical trial based on the assessment. The output (e.g., assessment) can further include, for example, the digital pathology image classification of the various image features (e.g., histologies, mutations, etc.), an interactive interface, or the derivative characteristics and statistics thereon. These output and more can be provided to a user via, for example, a suitably configured user device 330. The output can be provided in an interactive interface, that facilitates the user reviewing the analysis performed by the digital pathology image processing system 310 while also supporting the user's independent analysis. For example, the user can turn various features of the output on or off, zoom, pan, and otherwise manipulate the digital pathology image, and provide feedback or notes regarding the classifications, annotations, and derivative characteristics.

At step 750, the digital pathology image processing system 310 can optionally receive feedback regarding the provided subject assessment. The user can provide feedback regarding the accuracy of the classifications or annotations of the labels. The user can, for example, indicate areas of interest to the user (as well as the reason why they are interesting) that were not previously identified by the digital pathology image processing system 310. The user can additionally indicate additional classifications for the image that were not already suggested or captured by the digital pathology image processing system 310. This feedback can also be stored for the user's later access, for example as clinical notes.

At step 755, the digital pathology image processing system 310 can optionally use the feedback to retrain or update one or more of the machine-learning models, for example, the deep-learning neural networks or classification networks, used in the classification of the digital pathology images. The digital pathology image processing system 310 can use the feedback to supplement the training dataset available to the digital pathology image processing system 310 with the additional benefit that the feedback has been provided by a human expert which increases its reliability. The digital pathology image processing system 310 can continuously revise the deep-learning neural networks underlying the analysis provided by the system with a goal of increasing the accuracy of its classifications as well as increasing the rale at which the digital pathology image processing system 310 identifies major areas of interest. Thus, the digital pathology image processing system 310 is not a static system, but can offer and benefit from continuous improvement.

Particular embodiments may repeat one or more steps of the method of FIG. 7, when appropriate. Although this disclosure describes and illustrates particular steps of the method of FIG. 7 as occurring in a particular order, this disclosure contemplates any suitable steps of the method of FIG. 7 occurring in any suitable order. Moreover, although this disclosure describes and illustrates an example method for identifying features in a digital pathology image using a machine-learning model and generating a subject assessment based on heterogeneity of the identified features in the digital pathology image including the particular steps of the method of FIG. 7, this disclosure contemplates any suitable method for identifying features in a digital pathology image using a machine-learning model and generating a subject assessment based on heterogeneity of the identified features in the digital pathology image including any suitable steps, which may include all, some, or none of the steps of the method of FIG. 7, where appropriate. Furthermore, although this disclosure describes and illustrates particular components, devices, or systems carrying out particular steps of the method of FIG. 7, this disclosure contemplates any suitable combination of any suitable components, devices, or systems carrying out any suitable steps of the method of FIG. 7.

Figure 8:
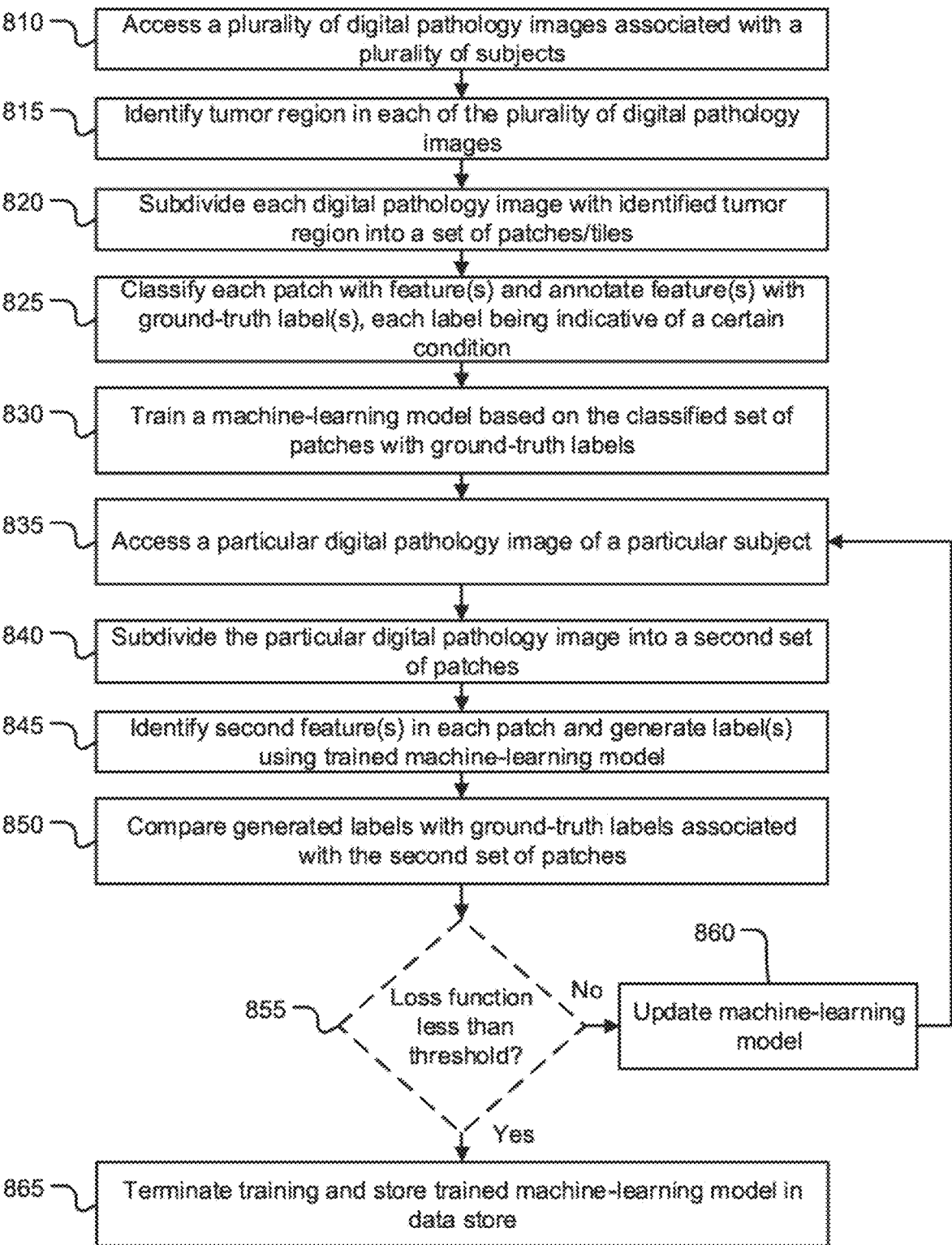
FIG. 8 illustrates an example method for training and updating a machine-learning model for labelling or classifying patches of a digital pathology image according to detection of image features depicted in the patches.

FIG. 8 illustrates an example method 800 for training and updating a machine learning model for labelling or classifying patches of a digital pathology image according to detection of image features depicted in the patches. In particular embodiments, steps 810-830 of the method 800 are associated with training the machine-learning model and steps 835-865 of the method 800 are associated with testing and updating the trained machine-learning model. The method 800 can begin at step 910, where the digital pathology image processing system 310 accesses a plurality of digital pathology images that are respectively associated with a plurality of subjects or patients. In particular embodiments, this includes receiving image data of tissue samples from non-small cell lung cancer (NSCLC) patients. By way of an example, 476 tissue samples from NSCLC patients that were scanned at 0.5 pixel/um resolution may be used as training dataset for training the machine-learning model discussed herein.

At step 815, the digital pathology image processing system 310 performs tumor lesion segmentation e.g., identities a tumor region in each of the plurality of digital pathology images accessed in step 810. As an example, a tumor region 515 may be identified in each of the images, as shown in FIG. 5A. In one embodiment, the tumor region may be automatically identified using a separate tumor lesion segmentation algorithm or one or more machine-learning techniques. For instance, a machine-learning model may be trained based on pre-labeled or pre-annotated tumor regions in a set of digital pathology images by human exports. In one embodiment, the tumor region may be manually selected by a user, such as a pathologist, a doctor, a clinical specialist, an expert in diagnosing lung cancers, etc.

At step 820, the digital pathology image processing system 310 may subdivide each digital pathology image with identified tumor region into a set of patches. For example, as shown in FIG. 5A, the digital pathology image processing system 310 may subdivide each image into a set of patches, such as set 535, set 536, set 537, and so on. In some embodiments, the size and shape of each patch is uniform for the purposes of analysis, but the size and shape can be variable. As an example, each digital pathology image with identified tumor region or area is subdivided into smaller image patches of 512×512 pixels. As described earlier, this disclosure contemplates any suitable steps of the training process 500 of FIG. 5A or method 800 of FIG. 8 occurring in any suitable order. For instance, in one embodiment, step 820 can occur before step 815. In another embodiment, the steps of the method 800 are performed in the order as illustrated in FIG. 8.

At step 825, the vet of patches extracted in step 820 may be classified or annotated with image features along with corresponding labels. For instance, one or more human experts or pathologists may classify one or mans features in each patch and annotate the features with one or more ground-truth labels indicative of a certain condition within a tissue sample. By way of an example, without limitation, each patch may be classified or labelled as including a particular histology, such as ADC or SCC, within a tissue sample. By way of another example, without limitation, each patch may be classified or labelled as including a particular mutation or gene variant, such as KRAS, ALK, TP53, within a tissue sample. This process may be repeated until all the extracted patches are annotated or labeled.

At step 830, the digital pathology image processing system 310 may train a machine-learning model (e.g., deep-learning neural network) based on the labeled set of patches. For instance, the training controller 317 may feed each labeled patch (e.g., classified tissue structure feature(s) with corresponding ground-truth label(s)) into the machine-learning model for training, us shown for example in FIG. 5A. In particular embodiments, the machine-learning model is a convolutional neural network that may be trained based on Inception V3 and Resnet18 architecture using transfer learning and weakly-supervised learning techniques. It should be understood that other learning techniques for training the machine-learning model are also possible and within the scope of the present disclosure. Once trained, the machine-learning model may be able to classify tissue patches using whole-slide level labels.

At step 835, the digital pathology image processing system 310 may access a particular digital pathology image of a particular subject for testing the trained machine-learning model. For instance, once the machine-learning model is trained based on the plurality of digital pathology images and corresponding patch labels as discussed above in steps 810-830, the trained machine-learning model may be tested on one or more unseen test slides or digital pathology images to verify an accuracy of the trained machine-learning model in its classification and determining a confidence in the model. As an example, the trained machine-learning model may be made to perform its testing on 20 unseen test slides for the verification. The test slides or images for testing the machine-learning model may be any number and may be preset by a user.

At step 840, the digital pathology image processing system 310 may subdivide the particular digital pathology image into a second set of patches as discussed elsewhere, herein and shown for example in FIG. 5B. At step 845, the digital pathology image processing system 310 may identify one or more second image features in each patch and generate one or more labels (e.g., histology subtype, mutation type, etc.) using the trained machine-learning model.

At step 850, the digital pathology image processing system 310 may compare the labels generated by the trained machine-teaming model with ground-truth labels or true labels. In some embodiments, the digital pathology image processing system 310 may compute a loss function based on the comparison. For instance, the training controller 310 may compare predicted labels for the second set of patches by the machine-learning model with true labels for these patches by human experts or pathologists to determine the loss function. In some embodiments, the loss function may be an indicator of an accuracy of the machine-learning model in predicting labels far features depicted within a given tissue sample. In some embodiments, the loss function may indicate an offset value quantifying how off the predicted labels by the machine-learning model are from the ground-truth or true labels. A comparison of predicted labels with true labels is shown, for example, in FIG. 6.

At step 855, the digital pathology image processing system 310 may optionally make a determination as to whether a scoring function (e.g., a loss function) computed based on the comparison in step 850 is less than a certain threshold. The threshold may be an upper limit set by a user (e.g., a pathologist) up to which the predicted labels by the machine-teaming models for the second set of patches are considered close or equivalent to the true or ground-truth labels. Stated differently, the threshold may be a limit or value, where if the scoring function indicating an offset value (e.g., quantifying how off the predicted labels by the machine-learning model are from the ground-truth or true labels) is less than or within the threshold value, the machine-learning model may be determined as accurate in its label prediction or classification. Whereas if the offset value of the scoring function is greater than the threshold value, the machine-teaming model is determined as inaccurate and flagged as requiring more training. By way of a non-limiting example, the threshold may be 90% and if the comparison between the predicted labels and true labels reveals that the concordance between the labels is 92% or that 92% of the predicted labels matches with the true labels, the machine-learning model may be deemed accurate and sufficiently trained. Continuing the same example, if the concordance between the predicted and true labels is only 75%, then the machine-learning model is determined as more training required or needed. In some embodiments, the training controller 317 may use comparison data, as shown for example in FIG. 6, to make this determination in step 855.

At step 860, the digital pathology image processing system 310 may update the machine-learning model. In certain embodiments, the updating occurs in response to determining that the scoring function is less than the threshold. In some embodiments, updating the machine-learning model may include one or more of repeating steps 810-830, reconfiguring or updating one or more parameters of the machine-learning model, and performing steps 835-855 to check whether the loss function meets threshold criteria (e.g., loss function is greater than the threshold value, concordance between predicted and true labels is greater than 90%, etc.). In particular embodiments, the updates are made in an effort to optimize the loss function or to minimize the difference between the generated/predicted labels and the true/ground-truth labels.

At step 865, the digital pathology image processing system 310 may terminate the training and store the trained machine-learning model in a data store for future access and/or retrieval in classification of features (e.g., histologies, mutations, etc.) in tissue samples. In some embodiments, the training controller 317 determines when to cease training. The determination may be based on predetermined termination rules. In some embodiments, the training may terminate in response to determining that the scoring function meets the threshold criteria or is greater than the threshold, in particular embodiments, the training may terminate once a predetermined number (e.g., 1000, 10,000, etc.) of training samples have been used to train the model. In particular embodiments, training may terminate once the training samples in the training dataset have all been used to train the model. In particular embodiments, training may terminate when the loss comparison (e.g., offset value of the loss function) is sufficiently small or below a predetermined threshold. If the training controller 317 determines that training should continue, the process may repeat from step 810. If instead, the training controller 317 determines that training should terminate, training would terminate.

Particular embodiments may repeat one or more steps of the method of FIG. 8, where appropriate. Although this disclosure describes and illustrates particular steps of the method of FIG. 8 as occurring in a particular order, this disclosure contemplates any suitable steps of the method of FIG. 8 occurring in any suitable order. Moreover, although this disclosure describes and illustrates an example method for training and updating a machine-learning model for labelling or classifying patches of a digital pathology image according to detect ion of image features depicted in the patches including the particular steps of the method of FIG. 8, this disclosure contemplates any suitable method for training and updating a machine-learning model for labelling or classifying patches of a digital pathology image according to detection of image features depicted in the patches including any suitable steps, which may include all, some, or none of the steps of the method of FIG. 8, where appropriate. Furthermore, although this disclosure describes and illustrates particular components devices, or systems carrying out particular steps of the method of FIG. 8, this disclosure contemplates any suitable combination of any suitable components, devices, or systems carrying out any suitable steps of the method of FIG. 8.

The general techniques described herein can be integrated into a variety of tools and use cases. For example, as described, a user (e.g., pathology or clinician) can access a user device 330 that is in communication with the digital pathology image processing system 310 and provide a digital pathology image for analysis. The digital pathology image processing system 310, or the connection to the digital pathology image processing system can be provided as a standalone software tool or package that automatically annotates digital pathology images and/or generates heat-maps evaluating the images under analysis. As a standalone tool or plug-in that can be purchased or licensed on a streamlined basis, the tool can be used to augment the capabilities of a research or clinical lab. Additionally, the tool can be integrated into the services made available to the customer of digital pathology image generation systems. For example, the tool can be provided as a unified workflow, where a user who conducts or requests a digital pathology image to be created automatically receives an annotated image or heatmap equivalent. Therefore, in addition to improving digital pathology image analysis, the techniques can be integrated into existing systems to provide additional features not previously considered or possible.

Moreover, the digital pathology image processing system 310 can be trained and customized for use in particular settings. For example, the digital pathology image processing system 310 can be specifically trained for use in providing clinical diagnoses relating to specific types of tissue (e.g., lung, heart, blood, liver, etc.). As another example, the digital pathology image processing system 310 can be trained to assist with safety assessment, for example in determining levels or degrees of toxicity associated with drugs or other potential therapeutic treatments. Once trained for use in a specific subject matter or use case, the digital pathology image processing system 310 is not necessarily limited to that use ease. For example, the digital pathology image processing system may be trained for use in toxicity assessment for liver tissues, but the resulting models can be applied to a diagnostic setting. Training may be performed in a particular context, e.g., toxicity assessment, due to a relatively larger set of at least partially labeled or annotated digital pathology images.

Figure 9:
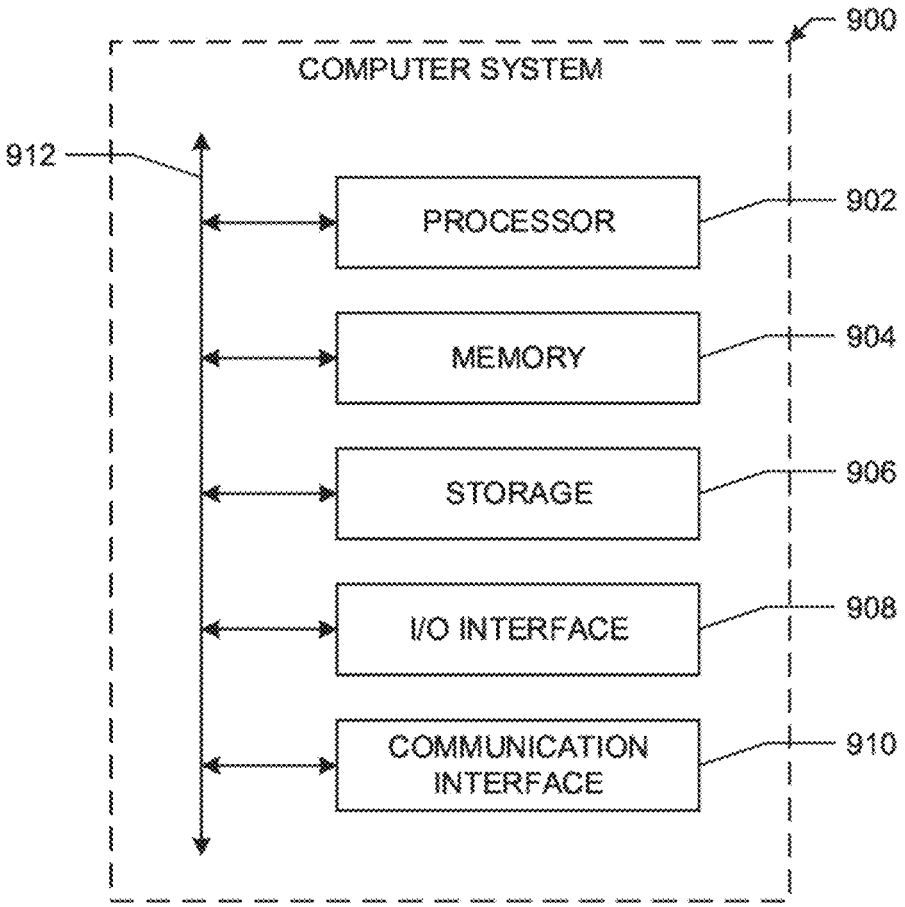
FIG. 9 illustrates an example computer system.

FIG. 9 illustrates an example computer system 900. In particular embodiments, one or more computer systems 900 perform one or mom steps of one or more methods described or illustrated herein. In particular embodiments, one or more computer systems 900 provide functionality described or illustrated herein. In particular embodiments, software running on one or more computer systems 900 performs one or more steps of one or more methods described or illustrated herein or provides functionality described or illustrated herein. Particular embodiments include one or more portions of one or more computer systems 900. Herein, reference to a computer system may encompass a computing device, and vice versa, where appropriate. Moreover, reference to a computer system may encompass one or more computer systems, where appropriate.

This disclosure contemplates any suitable number of computer systems 900. This disclosure contemplates computer system 900 taking any suitable physical form. As example and not by way of limitation, computer system 900 may be an embedded computer system, a system-on-chip (SOC), a single-board computer system (SBC) (such as, for example, a computer-on-module (COM) or system-on-module (SOM)), a desktop computer system, a laptop or notebook computer system, an interactive kiosk, a mainframe, a mesh of computer systems, a mobile telephone, a personal digital assistant (PDA), a server, a tablet computer system, an augmented/virtual reality device, or a combination of two or more of these. Where appropriate, computer system 900 may include one or more computer systems 900; be unitary or distributed; span multiple locations; span multiple machines; span multiple data centers; or reside in a cloud, which may include one or more cloud components in one or more networks. Where appropriate, one or more computer systems 900 may perform without substantial spatial or temporal limitation one or more steps of one or more methods described or illustrated herein. As an example and not by way of limitation, one or more computer systems 900 may perform in real time or in batch mode one or more steps of one or more methods described or illustrated herein. One or more computer systems 900 may perform at different times or at different locations one or more steps of one or more methods described or illustrated herein, where appropriate.

In particular embodiments, computer system 900 includes a processor 902, memory 904, storage 906, an input/output (I/O) interface 908, a communication interface 910, and a bus 912. Although this disclosure describes and illustrates a particular computer system having a particular number of particular components in a particular arrangement, this disclosure contemplates any suitable computer system having any suitable number of any suitable components in any suitable arrangement.

In particular embodiments, processor 902 includes hardware for executing instructions, such as those making up a computer program. As an example and not by way of limitation, to execute instructions, processor 902 may retrieve (or fetch) the instructions from an internal register, an internal cache, memory 904, or storage 906; decode and execute them; and then write one or more results to an internal register, an internal cache, memory 904, or storage 906. In particular embodiments, processor 902 may include one or more internal caches for data, instructions, or addresses. This disclosure contemplates processor 902 including any suitable number of any suitable internal caches, where appropriate. As an example and not by way of limitation, processor 902 may include one or more instruction caches, one or more data caches, and one or more translation lookaside buffers (TLBs). Instructions in the instruction caches may be copies of instructions in memory 904 or storage 906, and the instruction caches may speed up retrieval of those instructions by processor 902. Data in the data caches may be copies of data in memory 904 or storage 906 for instructions executing at processor 902 to operate on; the results of previous instructions executed at processor 902 for access by subsequent instructions executing at processor 902 or for writing to memory 904 or storage 906;

or other suitable data. The data caches may speed up read or write operations by processor 902. The TLBs may speed up virtual-address translation for processor 902. In particular embodiments, processor 902 may include one or more internal registers for data, instructions, or addresses. This disclosure contemplates processor 902 including any suitable number of any suitable internal registers, where appropriate. Where appropriate, processor 902 may include one or more arithmetic logic units (ALUs); be a multi-core processor; or include one or more processors 902. Although this disclosure describes and illustrates a particular processor, this disclosure contemplates any suitable processor.

In particular embodiments, memory 904 includes main memory for storing instructions for processor 902 to execute or data for processor 902 to operate on. As an example and not by way of limitation, computer system 900 may load instructions from storage 906 or another source (such as, for example, another computer system 900) to memory 904. Processor 902 may then load the instructions from memory 904 to an internal register or internal cache. To execute the instructions, processor 902 may retrieve the instructions from the internal register or internal cache and decode them. During or after execution of the instructions, processor 902 may write one or more results (which may be intermediate or final results) to the internal register or internal cache. Processor 902 may then write one or more of those results to memory 904. In particular embodiments, processor 902 executes only instructions in one or more internal registers or internal caches or in memory 904 (as opposed to storage 906 or elsewhere) and operates only on data in one or mote internal registers or internal caches or in memory 904 (as opposed to storage 906 or elsewhere). One or more memory buses (which may each include an address bus and a data bus) may couple processor 902 to memory 904. Bus 912 may include one or more memory buses, as described below. In particular embodiments, one or more memory management units (MMUs) reside between processor 902 and memory 904 and facilitate accesses to memory 904 requested by processor 902. In particular embodiments, memory 904 includes random access memory (RAM). This RAM may be volatile memory, where appropriate. Where appropriate, this RAM may be dynamic RAM (DRAM) or static RAM (SRAM). Moreover, where appropriate, this RAM may be single-ported or multi-ported RAM. This disclosure contemplates any suitable RAM. Memory 904 may include one or more memories 904, where appropriate. Although this disclosure describes and illustrates particular memory, this disclosure contemplates any suitable memory.

In particular embodiments, storage 906 includes mass storage for data or instructions. As an example and not by way of limitation, storage 906 may include a hard disk drive (HDD), a floppy disk drive, flash memory, an optical disc, a magneto-optical disc, magnetic tape, or a Universal Serial Bus (USB) drive or a combination of two or more of these. Storage 906 may include removable or non-removable (or fixed) media, where appropriate. Storage 906 may be internal or external to computer system 900, where appropriate. In particular embodiments, storage 906 is non-volatile, solid-state memory. In particular embodiments, storage 906 includes read-only memory (ROM). Where appropriate, this ROM may be mask-programmed ROM, programmable ROM (PROM), erasable PROM (EPROM), electrically erasable PROM (EEPROM), electrically alterable ROM (EAROM), or flash memory or a combination of two or more of these. This disclosure contemplates mass storage 906 taking any suitable physical form. Storage 906 may include one or more storage control units facilitating communication between processor 902 and storage 906, where appropriate. Where appropriate, storage 906 may include one or more storages 906. Although this disclosure describes and illustrates particular storage, this disclosure contemplates any suitable storage.

In particular embodiments, I/O interface 908 includes hardware, software, or both, providing one or more interfaces for communication between computer system 900 and one or more I/O devices. Computer system 900 may include one or marc of these I/O devices, where appropriate. One or more of these I/O devices may enable communication between a person and computer system 900. As an example and not by way of limitation, an I/O device may include a keyboard, keypad, microphone, monitor, mouse, printer, scanner, speaker, still camera, stylus, tablet, touch screen, trackball, video camera, another suitable I/O device or a combination of two or more of these. An I/O device may include one or more sensors. This disclosure contemplates any suitable I/O devices and any suitable I/O interfaces 908 for them. Where appropriate, I/O interface 908 may include one or more device or software drivers enabling processor 902 to drive one or more of these I/O devices. I/O interface 908 may include one or more I/O interfaces 908, where appropriate. Although this disclosure describes and illustrates a particular I/O interface, this disclosure contemplates any suitable I/O interface.

In particular embodiments, communication interface 910 includes hardware, software, or both providing one or more interfaces for communication (such as, for example, packet-based communication) between computer system 900 and one or more other computer systems 900 or one or mom networks. As an example and not by way of limitation, communication interface 910 may include a network interface controller (NIC) or network adapter for communicating with an Ethernet or other wire-based network or a wireless NIC (WNIC) or wireless adapter for communicating with a wireless network, such as a WI-FI network. This disclosure contemplates any suitable network and any suitable communication interface 910 for it. As an example and not by way of limitation, computer system 900 may communicate with an ad hoc network, a personal area network (PAN), a local area network (LAN), a wide area network. (WAN), a metropolitan area network (MAN), or one or more portions of the Internet or a combination of two or more of these. One or more portions of one or more of these networks may be wired or wireless. As an example, computer system 900 may communicate with a wireless PAN (WPAN) (such as, for example, a BLUETOOTH WPAN), a WI-FI network, a WI-MAX network, a cellular telephone network (such as, for example, a Global System for Mobile Communications (GSM) network), or other suitable wireless network or a combination of two or more of these. Computer system 900 may include any suitable communication interface 910 for any of these networks, where appropriate. Communication interface 910 may include one or more communication interfaces 910, where appropriate. Although this disclosure describes and illustrates a particular communication inter-lace, this disclosure contemplates any suitable communication interface.

In particular embodiments, bus 912 includes hardware, software, or both coupling components of computer system 900 to each other. As an example and not by way of limitation, bus 912 may include an Accelerated Graphics Port (AGP) or other graphics bus, an Enhanced Industry Standard Architecture (EISA) bus, a front-side bus (FSB), a HYPERTRANSPORT (HT) interconnect, an Industry Standard Architecture (ISA) bus, an INFINIBAND interconnect, a low-pin-count (LPC) bus, a memory bus, a Micro Channel Architecture (MCA) bus, a Peripheral Component Interconnect (PCI) bus, a PCI-Express (PCIe) bus, a serial advanced technology attachment (SATA) bus, a Video Electronics Standards Association local (VLB) bus, or another suitable bus or a combination of two or more of these. Bus 912 may include one or more buses 912, where appropriate. Although this disclosure describes and illustrates a particular bus, this disclosure contemplates any suitable bus or interconnect.

Herein, a computer-readable non-transitory storage medium or media may include one or more semiconductor-based or other integrated circuits (ICs) (such, as for example, field-programmable gate arrays (FPGAs) or application-specific ICs (ASICs)), hard disk drives (HDDs), hybrid hard drives (HHDs), optical discs, optical disc drives (ODDs), magneto-optical discs, magneto-optical drives, floppy diskettes, floppy disk drives (FDDs), magnetic tapes, solid-state drives (SSDs), RAM-drives, SECURE DIGITAL cards or drives, any other suitable computer-readable non-transitory storage media, or any suitable combination of two or more of these, where appropriate. A computer-readable non transitory storage medium may be volatile, non volatile, or a combination of volatile and non-volatile, where appropriate.

Herein, "or" is inclusive and not exclusive, unless expressly indicated otherwise or indicated otherwise by context. Therefore, herein, "A or B" means "A, B, or both," unless expressly indicated otherwise or indicated otherwise by context. Moreover, "and" is both joint and several, unless expressly indicated otherwise or indicated otherwise by context. Therefore, herein, "A and B" means "A and B, jointly or severally," unless expressly indicated otherwise or indicated otherwise by context.

The scope of this disclosure encompasses all changes, substitutions, variations, alterations, and modifications to the example embodiments described or illustrated herein that a person having ordinary skill in the art would comprehend. The scope of this disclosure is not limited to the example embodiments described or illustrated herein. Moreover, although this disclosure describes and illustrates respective embodiments herein as including particular components, elements, feature, functions, operations, or steps, any of these embodiments may include any combination or permutation of any of the components, elements, features, functions, operations, or steps described or illustrated anywhere herein that a person having ordinary skill in the art would comprehend. Furthermore, reference in the appended claims to an apparatus or system or a component of an apparatus or system being adapted to arranged to, capable of, configured to, enabled to, operable to, or operative to perform a particular function encompasses that apparatus, system, component, whether or not it or that particular function is activated, turned on, or unlocked, as long as that apparatus, system, or component is so adapted, arranged, capable, configured, enabled, operable, or operative. Additionally, although this disclosure describes or illustrates particular embodiments as providing particular advantages, particular embodiments may provide none, some, or all of these advantages.

What is claimed is:

1. A computer-implemented method comprising:

receiving a digital pathology image of a tissue sample from a patient;

subdividing the digital pathology image into a plurality of patches;

for each patch of the plurality of patches:

identifying a plurality of image features detected in the patch; and generating a plurality of labels corresponding to the plurality of image features identified in the patch using a trained machine-learning model, wherein the plurality of labels comprising one or more labels of a first label type and one or more labels of a second label type;

determining, based on a relative frequency of the first label type relative to the second label type in the generated plurality of labels, a heterogeneity metric for the tissue sample, wherein the heterogeneity metric quantifies a degree of heterogeneity of the tissue sample;

generating an assessment of the tissue sample based on the heterogeneity metric, wherein the assessment comprises a prediction of a responsiveness of the patient to one or more treatments;

generating a patch-based signature based on the generated plurality of labels; and using the patch-based signature, generating a visualization of image features for evaluating the trained machine-learning model.

2. The method of claim 1, wherein the digital pathology image of the tissue sample is a whole-slide image of a tumor sample from the patient, wherein the patient is diagnosed with non-small cell lung cancer.

3. The method of claim 1, wherein the digital pathology image is a hematoxylin and eosin (H&E) stained image.

4. The method of claim 1, wherein the image features detected in the patch of the digital pathology image correspond to histologies.

5. The method of claim 4, wherein the generated plurality of labels correspond to adenocarcinoma and squamous cell carcinoma cancer regions.

6. The method of claim 1, wherein the image features detected in the plurality of patches of the digital pathology image correspond to mutations or gene variants.

7. The method of claim 6, wherein the generated plurality of labels correspond to Kirsten rat sarcoma viral oncogene homolog (KRAS) mutation, epidermal growth factor receptor (EGFR) mutation, anaplastic lymphoma kinase (ALK) mutation, or tumor protein (TP53) mutation.

8. The method of claim 1, wherein the heterogeneity metric quantifies a degree of heterogeneity of the identified image features and corresponding labels in the tissue sample.

9. The method of claim 1, wherein the patch-based signature includes a heatmap, the heatmap comprising a plurality of regions, each region of the plurality of regions being associated with an intensity value, respectively, wherein one or more regions of the plurality of regions are further associated with a predicted label of the patch of the digital pathology image.

10. The method of claim 1, wherein the visualization of the image features identified in the tissue sample comprises displaying each of the generated plurality of labels in differentiated color coding.

11. The method of claim 1, wherein the patch-based signature is generated using a saliency mapping technique.

12. The method of claim 1, further comprising training the machine-learning model, wherein training the machine-learning model comprises:

accessing a plurality of digital pathology images associated with a plurality of subjects, respectively;

identifying a tumor region in each of the plurality of digital pathology images;

subdividing each of the plurality of digital pathology images into a set of training patches, wherein each training patch in the set is classified with one or more features and annotated with one or more ground-truth labels corresponding to the one or more features; and using classified set of training patches with ground-truth labels corresponding to the features depicted in the patches to train the machine-learning model.

13. The method of claim 12, wherein the ground-truth labels are provided by a clinician.

14. The method of claim 12, further comprising updating the machine-learning model, wherein updating the machine-learning model comprises:

accessing a particular digital pathology image of a particular subject;

subdividing the particular digital pathology image into a second set of patches;

identifying second images features in the second set of patches;

generating a set of predicted labels corresponding to the second image features identified in the second set of patches using the trained machine-learning model;

comparing the generated set of predicted labels with the ground-truth labels to measure an accuracy in label prediction of the machine-learning model; and updating the machine-learning model based on the comparison, wherein updating the machine-learning model comprises further training the machine-learning model.

15. The method of claim 1, wherein the machine-learning model is a deep-learning neural network.

16. The method of claim 1, further comprising:

determining one or more treatment options for a patient based on the assessment.

17. A digital pathology image processing system comprising:

one or more processors; and one or more computer-readable non-transitory storage media coupled to one or more of the processors and comprising instructions operable when executed by one or more of the processors to cause the system to perform operations comprising:

receiving a digital pathology image of a tissue sample from a patient;

subdividing the digital pathology image into a plurality of patches;

for each patch of the plurality of patches:

identifying a plurality of image features detected in the patch; and generating a plurality of labels corresponding to the plurality of image features identified in the patch using a trained machine-learning model, wherein the plurality of labels comprising one or more labels of a first label type and one or more labels of a second label type;

determining, based on a relative frequency of the first label type relative to the second label type in the generated plurality of labels, a heterogeneity metric for the tissue sample, wherein the heterogeneity metric quantifies a degree of heterogeneity of the tissue sample;

generating an assessment of the tissue sample based on the heterogeneity metric, wherein the assessment comprises a prediction of a responsiveness of the patient to one or more treatments;

generating a patch-based signature based on the generated plurality of labels; and using the patch-based signature, generating a visualization of image features for evaluating the machine-learning model.

18. The digital pathology image processing system of claim 17, wherein the image features detected in the patch of the digital pathology image correspond to histologies or mutations.

19. One or more computer-readable non-transitory storage media including instructions that, when executed by one or more processors, are configured to cause the one or more processors of a digital pathology image processing system to perform operations comprising:

receiving a digital pathology image of a tissue sample from a patient;

subdividing the digital pathology image into a plurality of patches;

for each patch of the plurality of patches:

identifying a plurality of image features detected in the patch; and generating a plurality of labels corresponding to the plurality of image features identified in the patch using a trained machine-learning model, wherein the plurality of labels comprising one or more labels of a first label type and one or more labels of a second label type;

determining, based on a relative frequency of the first label type relative to the second label type in the generated plurality of labels, a heterogeneity metric for the tissue sample, wherein the heterogeneity metric quantifies a degree of heterogeneity of the tissue sample;

generating an assessment of the tissue sample based on the heterogeneity metric, wherein the assessment comprises a prediction of a responsiveness of the patient to one or more treatments;

generating a patch-based signature based on the generated plurality of labels; and using the patch-based signature, generating a visualization of image features for evaluating the machine-learning model.

* * * * *